(12) United States Patent
Rudolph et al.

(10) Patent No.: US 11,623,200 B2
(45) Date of Patent: Apr. 11, 2023

(54) REACTOR SYSTEMS

(71) Applicant: ABEC, Inc., Bethlehem, PA (US)

(72) Inventors: Eric Rudolph, Bethlehem, PA (US);
Pete Silverberg, Bethlehem, PA (US);
Barry Reiss, Bethlehem, PA (US);
Sarah Murrat, Bethlehem, PA (US);
Colton Mitchell, Bethlehem, PA (US)

( * ) Notice: Subject to any disclaimer, the term of this patent is extended or adjusted under 35 U.S.C. 154(b) by 339 days.

(21) Appl. No.: 16/652,600

(22) PCT Filed: Oct. 2, 2018

(86) PCT No.: PCT/US2018/053880
§ 371 (c)(1),
(2) Date: Mar. 31, 2020

(87) PCT Pub. No.: WO2019/070648
PCT Pub. Date: Apr. 11, 2019

(65) Prior Publication Data
US 2020/0230568 A1 Jul. 23, 2020

Related U.S. Application Data

(60) Provisional application No. 62/690,281, filed on Jun. 26, 2018, provisional application No. 62/675,935, (Continued)

(51) Int. Cl.
*B01J 19/18* (2006.01)
*C12M 1/00* (2006.01)
(Continued)

(52) U.S. Cl.
CPC .............. *B01J 19/18* (2013.01); *C12M 23/28* (2013.01); *C12M 41/22* (2013.01); *C12M 41/34* (2013.01);
(Continued)

(58) Field of Classification Search
CPC .............. B01J 19/18; B01J 2219/00085; B01J 2219/00094; B01J 2219/00159; B01J 2219/185; B01J 2219/00331; B01J 2219/00495; C12M 23/28; C12M 41/22; C12M 41/34
(Continued)

(56) References Cited

U.S. PATENT DOCUMENTS

| 131,875 A | 10/1872 | Hall et al. |
| 609,595 A | 8/1898 | Sprecher et al. |

(Continued)

FOREIGN PATENT DOCUMENTS

| CN | 108004122 A | 5/2018 |
| DE | 3340353 A1 | 5/1985 |

(Continued)

OTHER PUBLICATIONS

Examination Report for Singapore Application No. 11202003030R dated Mar. 18, 2022.
(Continued)

*Primary Examiner* — Huy Tram Nguyen
(74) *Attorney, Agent, or Firm* — Patrick J. Halloran

(57) ABSTRACT

This disclosure relates to reaction container systems providing for headspace-based condensation, coalescing devices, and other features.

15 Claims, 13 Drawing Sheets

Related U.S. Application Data filed on May 24, 2018, provisional application No. 62/640,210, filed on Mar. 8, 2018, provisional application No. 62/633,844, filed on Feb. 22, 2018, provisional application No. 62/567,567, filed on Oct. 3, 2017.

(51) Int. Cl.
  *C12M 1/02* (2006.01)
  *C12M 1/34* (2006.01)

(52) U.S. Cl.
  CPC ............... *B01J 2219/00085* (2013.01); *B01J 2219/00094* (2013.01); *B01J 2219/00159* (2013.01); *B01J 2219/185* (2013.01)

(58) Field of Classification Search
  USPC ....................................................... 435/297.1
  See application file for complete search history.

(56) References Cited

U.S. PATENT DOCUMENTS

| | | |
|---|---|---|
| 2,162,400 A | 6/1939 | Heath |
| 2,816,064 A | 10/1955 | Smith |
| 2,973,944 A | 3/1961 | Augustus |
| 3,056,664 A | 10/1962 | Dravnieks |
| 3,063,259 A | 11/1962 | Hankinson et al. |
| 3,173,763 A * | 3/1965 | Miller .................. B01J 14/00 196/14.52 |
| 3,174,830 A | 3/1965 | Watzl et al. |
| 3,177,932 A | 4/1965 | Smith, Jr. et al. |
| 3,212,274 A | 10/1965 | Eidus |
| 3,373,802 A | 3/1968 | Wiklund et al. |
| 3,380,513 A | 4/1968 | Staats, Jr. et al. |
| 3,400,051 A | 9/1968 | Hofschneider |
| 3,600,137 A | 8/1971 | Girantet et al. |
| 3,604,690 A | 9/1971 | Traelnes |
| 3,662,817 A | 5/1972 | Kendrick et al. |
| 3,762,212 A | 10/1973 | Morley et al. |
| 3,776,042 A | 12/1973 | Werra et al. |
| 3,779,082 A | 12/1973 | Galloway et al. |
| 3,978,918 A | 9/1976 | Nagatomo et al. |
| 3,986,934 A | 10/1976 | Muller |
| 4,029,143 A | 6/1977 | Goebel |
| 4,207,180 A | 6/1980 | Chang |
| 4,212,950 A | 7/1980 | Adams |
| 4,426,959 A | 1/1984 | McCurley |
| 4,460,278 A | 7/1984 | Matsubara et al. |
| 4,573,933 A | 3/1986 | Cameron |
| 4,588,024 A | 5/1986 | Murray et al. |
| 4,588,085 A | 5/1986 | Sussman |
| 4,670,397 A | 6/1987 | Wegner et al. |
| 4,847,203 A | 7/1989 | Smart |
| 4,919,906 A | 4/1990 | Barber |
| 4,932,533 A | 6/1990 | Collier |
| 4,941,531 A | 7/1990 | Moiseeff |
| 4,985,208 A | 1/1991 | Sugawara et al. |
| 4,995,945 A | 2/1991 | Craig |
| 5,174,928 A | 12/1992 | Cheng et al. |
| 5,220,535 A | 6/1993 | Brigham et al. |
| 5,309,750 A | 5/1994 | Riley |
| 5,372,621 A | 12/1994 | Staton et al. |
| 5,513,516 A | 5/1996 | Stauffer |
| 5,525,512 A | 6/1996 | Pieler et al. |
| 5,547,329 A | 8/1996 | Hirai et al. |
| 5,599,507 A | 2/1997 | Shaw et al. |
| 5,728,929 A | 3/1998 | Gevaud |
| 5,762,887 A | 6/1998 | Girod et al. |
| 5,907,093 A | 5/1999 | Lehmann et al. |
| 5,958,763 A | 9/1999 | Goffe |
| 5,985,347 A | 11/1999 | Ejnik |
| 5,989,500 A | 11/1999 | Peacock et al. |
| 6,133,021 A | 10/2000 | Gu et al. |
| 6,254,143 B1 | 7/2001 | Billmyer et al. |
| 6,460,405 B1 | 10/2002 | Mayer et al. |
| 6,557,255 B2 | 5/2003 | Billmyer et al. |
| 6,572,641 B2 | 6/2003 | Brugger et al. |
| 6,596,521 B1 | 7/2003 | Chang et al. |
| 6,664,095 B1 | 12/2003 | Suryanarayan et al. |
| 6,923,567 B2 | 8/2005 | Bibbo et al. |
| 6,955,793 B1 | 10/2005 | Arencibia, Jr. |
| 7,231,811 B2 | 6/2007 | Sagi et al. |
| 7,308,819 B2 | 12/2007 | Kamio et al. |
| 7,373,944 B2 | 1/2008 | Lehmann |
| 7,384,783 B2 | 6/2008 | Baxter |
| 7,478,535 B2 | 1/2009 | Turner |
| 7,565,828 B2 | 7/2009 | Barcan et al. |
| 7,629,167 B2 | 12/2009 | Hodge et al. |
| 7,682,067 B2 | 3/2010 | West et al. |
| 7,682,823 B1 | 3/2010 | Runyan et al. |
| 7,815,851 B1 | 10/2010 | Lewis et al. |
| 8,282,267 B2 | 10/2012 | Castillo et al. |
| 8,381,780 B2 | 2/2013 | Fisher et al. |
| 8,455,242 B2 | 6/2013 | Staheli et al. |
| 8,534,120 B1 | 9/2013 | Pavlik |
| 8,658,419 B2 | 2/2014 | Knight |
| 9,109,193 B2 | 8/2015 | Galliher et al. |
| 9,127,246 B2 | 9/2015 | Staheli et al. |
| 9,228,165 B2 | 1/2016 | Knight et al. |
| 9,284,524 B2 | 3/2016 | Staheli et al. |
| 9,499,781 B2 | 11/2016 | Damren et al. |
| 9,528,083 B2 | 12/2016 | Staheli et al. |
| 9,719,705 B2 | 8/2017 | Fricking et al. |
| 10,143,935 B2 | 12/2018 | Govindan et al. |
| 10,221,383 B2 | 3/2019 | Damren et al. |
| 10,711,233 B2 | 7/2020 | Staheli et al. |
| 2002/0105856 A1 | 8/2002 | Terentiev et al. |
| 2003/0209344 A1 | 11/2003 | Fang et al. |
| 2003/0219453 A1 | 11/2003 | Maisonneuve et al. |
| 2004/0154331 A1 | 8/2004 | Horiuchi et al. |
| 2004/0190372 A1 | 9/2004 | Goodwin et al. |
| 2005/0092181 A1 | 5/2005 | Shih et al. |
| 2005/0239198 A1 | 10/2005 | Kunas et al. |
| 2005/0247110 A1 | 11/2005 | Sagi et al. |
| 2005/0272146 A1 | 12/2005 | Hodge et al. |
| 2006/0137742 A1 | 6/2006 | Smith et al. |
| 2006/0201662 A1 | 9/2006 | Gelbert et al. |
| 2006/0277975 A1 | 12/2006 | Barcan |
| 2006/0280028 A1 | 12/2006 | West et al. |
| 2007/0096611 A1 | 5/2007 | Antonijevic et al. |
| 2007/0169916 A1 | 7/2007 | Wand et al. |
| 2008/0047259 A1 | 2/2008 | Frydman et al. |
| 2008/0139865 A1 | 6/2008 | Galliher et al. |
| 2008/0145924 A1 | 6/2008 | Kobiyashi et al. |
| 2008/0206847 A1 | 8/2008 | Kunis et al. |
| 2008/0262409 A1 | 10/2008 | Derrico et al. |
| 2009/0035856 A1 | 2/2009 | Galliher et al. |
| 2009/0111179 A1 | 4/2009 | Hata et al. |
| 2009/0145591 A1 | 6/2009 | Rericha et al. |
| 2009/0180933 A1 | 7/2009 | Kauling et al. |
| 2009/0290962 A1 | 11/2009 | Fisher et al. |
| 2009/0311776 A1 | 12/2009 | Kelly et al. |
| 2010/0062522 A1 | 3/2010 | Fanning et al. |
| 2010/0149908 A1 | 6/2010 | Singh et al. |
| 2010/0301042 A1 | 12/2010 | Kahlert |
| 2010/0303682 A1 | 12/2010 | Rizzi et al. |
| 2010/0326172 A1 | 12/2010 | Voute et al. |
| 2011/0011164 A1 | 1/2011 | Terentiev et al. |
| 2011/0013474 A1 | 1/2011 | Ludwig et al. |
| 2011/0059523 A1 | 3/2011 | Knight |
| 2011/0076759 A1 | 3/2011 | Reif et al. |
| 2011/0188928 A1 | 8/2011 | West et al. |
| 2012/0011867 A1 | 1/2012 | Koons et al. |
| 2012/0100605 A1 | 4/2012 | Kauling et al. |
| 2012/0218855 A1 | 8/2012 | Kunis et al. |
| 2013/0081995 A1 | 4/2013 | Larsen et al. |
| 2013/0171616 A1 | 7/2013 | Niazi |
| 2014/0248192 A1 | 9/2014 | Burton |
| 2014/0349385 A1 | 11/2014 | Erdenberger et al. |
| 2014/0366969 A1 | 12/2014 | Chaussin et al. |
| 2016/0230138 A1 | 8/2016 | Damren et al. |
| 2016/0272931 A1 | 9/2016 | Rudolph et al. |
| 2017/0051239 A1 | 2/2017 | Knight et al. |

(56) References Cited

U.S. PATENT DOCUMENTS

| | | |
|---|---|---|
| 2017/0349874 A1 | 12/2017 | Jaques et al. |
| 2018/0119084 A1 | 5/2018 | Tuohey et al. |
| 2018/0243679 A1 | 8/2018 | Faldt et al. |
| 2018/0272247 A1 | 9/2018 | Brown et al. |

FOREIGN PATENT DOCUMENTS

| | | |
|---|---|---|
| EP | 1172138 B1 | 7/2005 |
| EP | 1616938 A2 | 1/2006 |
| EP | 1854871 A1 | 11/2007 |
| EP | 2783743 A1 | 10/2014 |
| JP | 57125202 A2 | 8/1982 |
| JP | 6011408 A | 1/1994 |
| JP | 8082568 A | 3/1996 |
| WO | 9405991 A1 | 3/1994 |
| WO | 2008040568 A1 | 4/2008 |
| WO | PCTUS2018053880 | 5/2019 |

OTHER PUBLICATIONS

Notification of Grant for Singapore Application No. 11202003030R dated May 18, 2022.
The MAC Humidity/Moisture Handbook. Machine Applications Corporation (2011).
Purpose-built single-use fermentors. Thermo-Fisher Scientific (2016).
DHX Heat Exchanger, Thermo-Fisher Scientific (2016).
Xcellerex™ XDR-500 MO single-use fermentor system. GE Healthcare Bio-Sciences AB (2016).
Xcellerex™ XDR-50 MO single-use fermentor system. GE Healthcare Bio-Sciences AB (2016).
ASTM International—Designation No. F2391-05, ASTM F2391-05(2011) Standard Test Method for Measuring Package and Seal Integrity Using Helium as the Tracer Gas Current edition approved Apr. 1, 2005. Published May 2005 Copyright© ASTM International, 100 Barr Harbor Drive, PO Box C700, West Conshohocken, PA, 19428-2959 USA.
McCrea, et al., "Separation of Vaccinia Hemagglutinin from Infectious Virus Particles by Chromatography on DEAE Columns," Department of Biophysics, Yale University, 3 pgs, 1958.
Miyako, Yasuhiro et al, Helium Leak Test for Sterility Assurance of a Sealed Bag. I: Relationship of Helium Leak and Pinhole Diameter, PDA Journal of Pharmaceutical Science and Technology, Jul./Aug. 2002, pp. 183-191, vol. 56, No. 4, Osaka, Japan.
Miyako, Yasuhiro et al, Helium Leak Test for Sterility Assurance of a Sealed bag. II: Establishing a Test Method for the Manufacturing Process. DA Journal of Pharmaceutical Science and Technology, May/Jun. 2003, pp. 186-197, vol. 57, No. 3, Osaka, Japan.
Pethe et al. "Helium Integrity Testing—A New Way to Ensure Single-Use Bag Integrity," PharmPro.com, 2 pgs, 2011.
Tranter, Inc., Brochure—PlateCoil Heat Exchangers, Document PCC-5, 20 pgs, 2006.

\* cited by examiner

REACTOR VESSEL

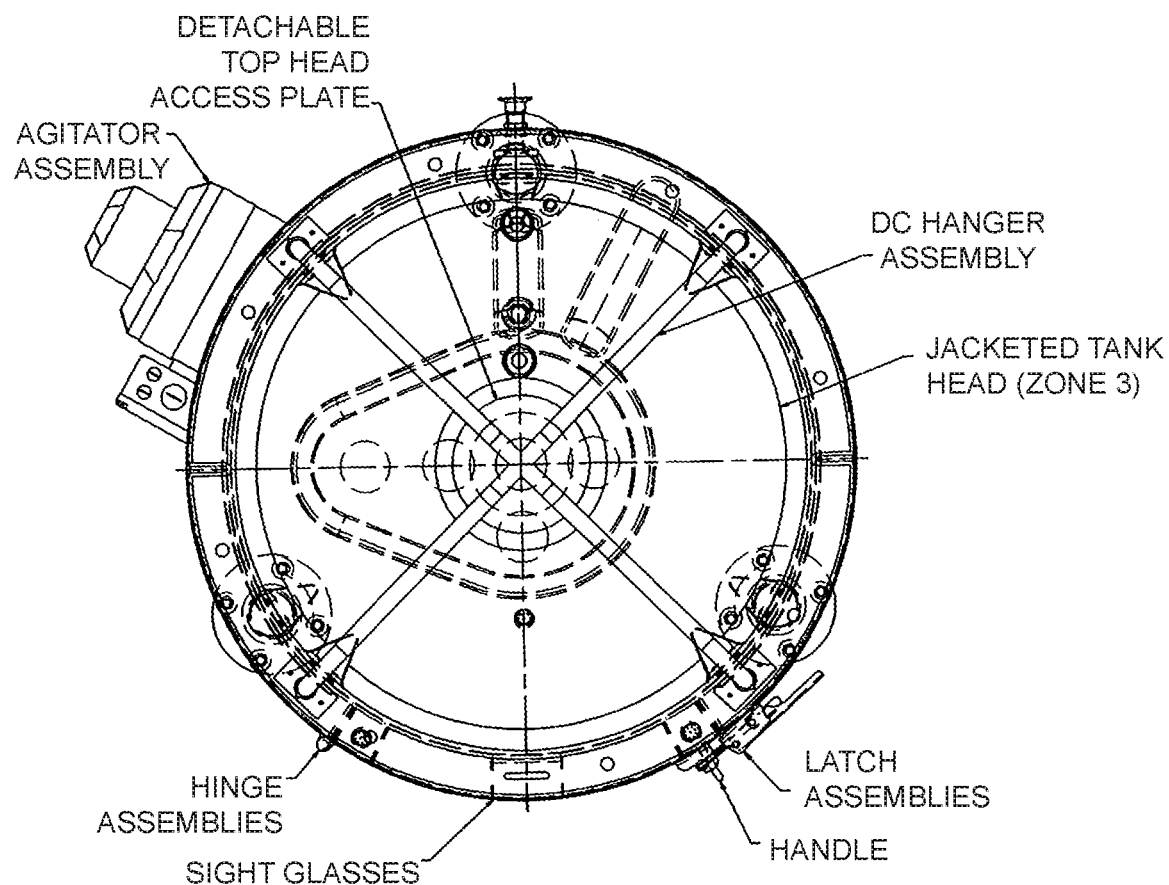

SIDE VIEW OF REACTOR VESSEL

PLAN VIEW

REACTOR SYSTEMS

RELATED APPLICATIONS

This application is a 35 U.S.C. § 371 national stage application of International Application No. PCT/US2018/053880, filed Oct. 2, 2018, and claims priority to U.S. Ser. No. 62/567,567 filed Oct. 3, 2017; U.S. Ser. No. 62/633,844 filed Feb. 22, 2018; U.S. Ser. No. 62/640,210 filed Mar. 8, 2018; U.S. Ser. No. 62/675,935 filed May 24, 2018; and U.S. Ser. No. 62/690,281 filed Jun. 26, 2018; each of which being hereby incorporated by reference in their entirety into this application.

FIELD OF THE DISCLOSURE

This disclosure relates to the reaction container systems (e.g., reactor systems) providing for headspace-based condensation, coalescing devices, and other features.

BACKGROUND OF THE DISCLOSURE

This disclosure relates to devices and methods for the manufacture of chemical and/or biological products such as biopharmaceuticals using reaction containers such as, e.g., multi-use ("MU") and/or disposable containers ("DC", e.g., single-use ("SU")) systems ("reaction container systems"). For instance, fermentors or bioreactors commonly provide a reaction vessel for cultivation of microbial organisms or mammalian, insect, or plant cells to produce such products. Common problems encountered by those using such systems include excessive moisture in the air exhausting therefrom; excess stress being placed on the upper section of a disposable container ("DC"; e.g., a section of continuous film and/or at a seam and/or weld; the headspace section); the need for a separate condenser unit external to the reactor in which a separate DC is contained (e.g., GE's Xcellerex and ThermoFisher's DHX system), requiring additional tubing and pumps and the like (e.g., exhaust tubing); and/or, maintaining the temperature of the reaction mixture within the reactor and/or DC during processing. This disclosure provides improved systems and parts that solve such problems. The systems described herein solve such problems by, for example, condensing fluid from said gas within the headspace (providing a "headspace condenser" or "HC") by providing a lower temperature therein as compared to the portion of the container in which the reaction is carried out, which provides for less load being placed on exhaust filters; including a jacketed and enclosed holder to remove heat across two zones of DC and providing additional physical support (e.g., a solid surface providing for heat transfer such that the temperature within the headspace is decreased) to the uppermost part of the DC (e.g., the holder dome), thereby relieving pressure thereupon and/or providing higher operating pressure capabilities thereto; directly associating the container (e.g., fermenter) with a coalescing unit such that condensation unit external to the reactor is not required; depositing/returning condensed fluid into the reaction mixture (e.g., passively by gravity) which provides both increased efficiency and additional temperature control; additionally or alternatively removing condensed fluid using cyclonic/mixing/contact forces causing coalescence of condensed vapor particles; and/or reducing the pressure on the DC film using an exhaust pump preferably pulling the exhaust from the headspace from the downstream side of a sterile barrier. Other problems and solutions to the same or other problems are described and/or may be derived from this disclosure, as described below.

BRIEF DESCRIPTION OF THE DRAWINGS

FIG. 1. Exemplary disposable container system.

FIG. 2. FIG. 2C provides a top view of an exemplary reactor vessel.

SUMMARY OF THE DISCLOSURE

Figure 1A:
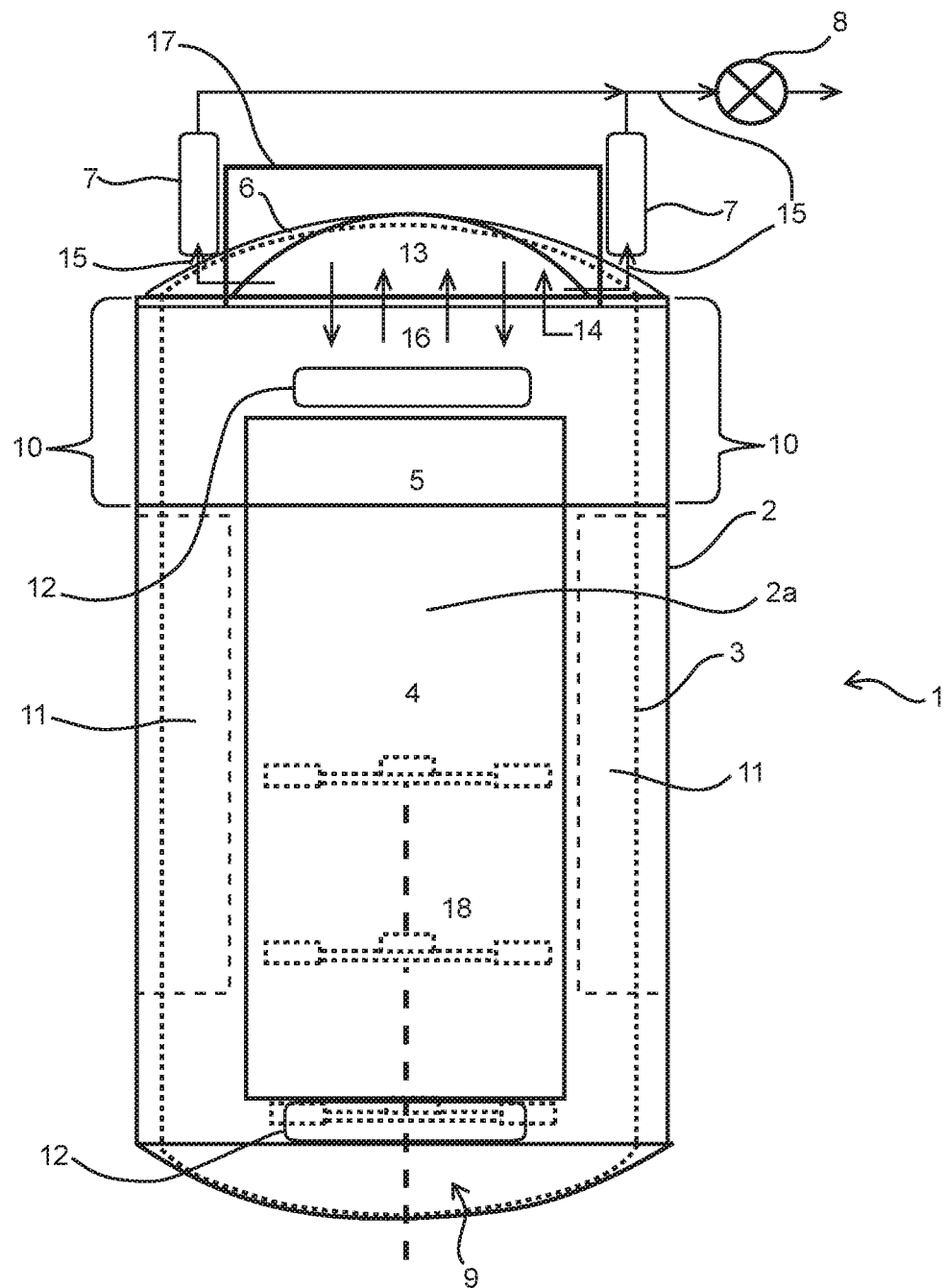
FIG. 1A provides a side view of an exemplary system.

This disclosure relates to multi-use ("MU") and disposable container ("DC", e.g., single-use ("SU")) systems ("reaction container systems") that, in some embodiments, comprise a disposable reaction container comprising first and second zones; the first zone comprising a reaction mixture maintained at a first temperature; the second zone being maintained at a second temperature lower than that of the first temperature, and comprising a headspace comprising an upper interior surface (opposite or adjacent to a corresponding exterior surface), and at least one sidewall; and, a coalescer for collecting fluid condensed in and escaping from the upper interior and/or at least one sidewall of the headspace; and methods for using the same. Other embodiments will be apparent from the disclosure provided herein.

DETAILED DESCRIPTION

This disclosure relates to reaction container systems such as multi-use ("MU") and/or disposable container ("DC", e.g., single-use ("SU")) systems that solve several art-recognized problems, some of which have been described above, and methods for using the same. In some embodiments, the systems may include a reaction vessel, a disposable container (e.g., a single-use diposable container ("SUDC") typically made of a flexible material such as a plastic), one or more filters, and/or one or more exhaust devices. These systems may also include a jacketed tank head, one or more coalescing units contacting the jacketed tank head, one or more additional condensing units, and/or one or more exhaust systems.

In some embodiments, the system comprises a single use disposable container (DC) comprising a film forming (e.g., surrounding) a headspace ("HS") in the DC which is maintained at a temperature lower than the portion of the DC in which a reaction is carried out (e.g., fluid reactants); and/or, a condenser directly associated with/in contact with the film forming the headspace; and/or a coalescing device enhancing liquid gathering (e.g., collection) and drainage from the headspace. In some embodiments, the DC system may comprise a DC comprising first and second zones; the first zone comprising a reaction mixture maintained at a first temperature; the second zone comprising a HS maintained at a second temperature lower than that of the first temperature, the HS comprising an upper interior surface (adjacent to or opposite an exterior surface) and at least one sidewall; and, a coalescer for collecting fluid condensed in and escaping from the upper interior surface and/or at least one sidewall of the HS. In some embodiments, a heat exchange device contacts the HS and/or is provided within the HS. In some preferred embodiments, the temperature difference may be about 5-10° C. (i.e., the first temperature can be 5-10° C. warmer than the second temperature or, in other words, the second temperature can be 5-10° C. cooler than the first temperature). In some embodiments, such a heat exchange device contacts the sidewall(s) and/or upper interior and/or exterior surface of the HS. In most and preferred embodiments, the DC is surrounded by a reaction vessel, which typically provides support to the DC and other components of the system.

In operating certain embodiments of the systems described herein, one or more dry gasses (e.g., air, $N_2$, $O_2$, $CO_2$) are introduced into the reaction mixture contained within the DC (the first zone) from the bottom (e.g., through a port positioned in or near the bottom or lower surface of the DC) and traverse through the liquid reaction mixture (e.g., toward) and into the second zone (HS). Along this path, the originally dry gas becomes a humid (or humidified or moist) gas (e.g., a vapor and/or mist). In some embodiments, the humid gas that emerges from the reaction mixture enters and passes through the second zone (HS), then to a coalescer, and then, typically and optionally, to and through a sterilizing filter. In some embodiments, some of the fluid contained in the humid gas is condensed in the second zone HS by virtue of the temperature difference between the first zone comprising the reaction mixture and the second zone (HS), and the remaining humid gas continues to migrate through and out of the HS and into the coalescer. The condensate collected in the cooled HS may then passively move (e.g., by gravity) back into the reaction mixture (as it is positioned below the HS in the DC), thereby lowering and/or maintaining the temperature of the reaction mixture to and/or at a desired temperature and/or temperature range. The coalescer serves to coalesce, or collect, any additional moisture (e.g., within any remaining humid gas) that has moved out of (or traversed through) the HS. This coalescing may be enhanced by, e.g., a further temperature difference between the HS and the coalescer (e.g., a lower temperature as compared to the HS, such as room temperature environment (e.g., 25° C.)) and/or other processes (e.g., cyclonic/mixing/contact forces causing coalescence of condensed vapor particles). The coalescer may also be further cooled (i.e., actively cooled), if desired, to a lower and/or particular temperature by association with (e.g., direct contact with) a heat exchange apparatus, which may be the same or different from that (i.e., heat exchange apparatus) cooling the second zone (HS), and may be and/or comprise, in some embodiments, a jacketed tank head. A further condensing unit may be included in the system, and this condensing unit may have a further lower temperature than either or both of the HS and/or the coalescer.

For example, in some embodiments, the first zone of the reaction container (i.e., the portion thereof comprising a liquid reaction mixture) may be maintained at an average temperature of 35-40° C. (i.e., a first temperature), such as 37° C., while the second zone (i.e., the HS) may be maintained at an average temperature of 30-34° C. (i.e., a second temperature) (e.g., 30° C., 32° C., 34° C.), and the coalescer may be maintained at a different temperature (e.g., an average temperature of 25° C. or room temperature; a third temperature being 5-10° C. cooler than the second temperature in the second zone and, accordingly, 10-15° C. cooler than the first temperature in the first zone). The temperature of the coalescer may also be affected by the jacketed tank head, upon which at least part of it typically rests (see, e.g., FIG. 1B). The optional further condensing unit described below may provide a further lower average temperature to further assist with condensation of fluid from the moist gas. "Average temperature" refers to the average of the temperature measured at, for instance, three different areas of the compartment of interest since, as would be understood by those of ordinary skill in the art, the temperature at such different areas may vary in the course of a reaction, but together provide an average temperature. The fluid collected in the coalescer may then passively move (e.g., by gravity) back into the second zone (HS), and/or into the first zone (containing the reaction mixture) (e.g., also passively by gravity), thereby lowering and/or maintaining the temperature of the reaction mixture at a desired temperature and/or temperature range. Any remaining gas (i.e., still humid gas), may then move out of the second zone (HS) and/or coalescer, through a filter (e.g., a sterile filter), and exit the system through an exhaust outlet. As described below, in some embodiments, the movement of gas through the headspace, into the coalescer, and out of the system may be assisted by an exhaust pump which, in some embodiments, may include one or more fans.

In some embodiments, the systems described herein include a reaction vessel. Reactions may be carried out in the reactor vessel per se, or in a container (e.g., a DC) contained within the reaction vessel. The reactions carried out in the systems described herein are typically carried out in a DC. The reaction vessel may take the form of a reaction chamber, fermentor, bioreactor, or the like. The reaction vessel is suitable for chemical reactions, fermentation of microbial organisms, cultivation of cells (e.g., mammalian, insect or plant-based), or other uses. The reaction vessel is typically associated with heat transfer system comprising a heat transfer apparatus for controlling the temperature of a chemical, pharmaceutical or biological process being carried out in within an internal reaction chamber of the vessel. In some embodiments, the heat transfer system provides for distribution of a heat transfer medium such that heat resulting from or required by the process is transferred from or to the reaction mixture. In some embodiments, the reaction vessel comprises a jacket and/or a jacketed tank head that provides a fluidic channel through which a heat transfer fluid may be circulated (e.g., a dimple jacket). In some embodiments, the reaction vessel may be a least partially surrounded by a fluidic channel. The jacketed tank head may also act as a lid for the reaction vessel. The jacketed tank head may also serve to support and/or relieve pressure on a DC (e.g., on the top of the DC) contained within the reactor vessel.

In some embodiments, instead of or in addition to a jacketed tank head, a flexible material cover and/or multiple straps (which may be comprised of such a flexible material) may be used to support and or relieve pressure on the DC (e.g., on the top of the DC) contained within the reactor vessel. In some embodiments, such a flexible material cover and/or straps may be positioned on the DC at one or more positions thereupon that may not be capable of withstanding pressure as well as another one or more positions on the DC (e.g., a seam in the material forming the DC). Straps may, for example, be positioned in a pattern traversing the external surface of the top of the DC in a pattern that supports and/or strengthens that surface (e.g., passing back and forth one or more times across the surface; a criscross pattern). Such straps may be constructed of any suitable material such as, but not limited to, a fabric, rubber, plastic, metal, and/or combination of the same, and may be flexible or inflexible. The flexible material cover and/or straps are typically affixed to the reactor vessel at one or more positions thereupon (e.g., the interior and/or exterior surface(s) thereof) using one or more connectors and/or a brackets (e.g., a tie connector, pipe grip tie). In some embodiments, each of the one or more straps has at least two ends, where each end is affixed (e.g., reversibly affixed) to the reactor vessel through connectors and/or brackets across the top diameter of the reactor vessel such that the strap(s) extends across one or more top diameters of the DC. In some embodiments, the straps may take the form of a net. In some embodiments, the straps form a flat strap cargo net that could cover part of or the entire top surface of the DC, or only those areas of that top surface that experience increased pressure (e.g., where force/pressure would concentrate), or exhibit weakness (e.g., at a seam) as compared to another area that is not subject to such pressure and/or exhibit such relative weakness. In some embodiments, the flexible material may be a light weight, nylon fabric (e.g., "parachute-type" fabric) which can be more conforming to the shape of the DC and less elastic than other materials, thereby ensuring a proper fit and adequate support. As such, the DC may be able to withstand greater forces (e.g., increased pressure) resulting from certain reactions taking place in the first zone of the DC. Some reactions may produce a volume of gas that produces pressure exceeding the capability of the DC and results in deformation of the DC (e.g., a burst in a seam); the tank head (e.g., jacketed tank head, one or more straps) will provide support for the DC, thereby increasing the pressure capabilities of the system. In some embodiments, it is preferred to use the jacketed tank head, flexible cover, and/or straps to maintain the pressure upon the top surface of the DC at more than 0.1-0.2 pounds per square inch (PSI). In some embodiments, the flexible supports and/or straps can also facilitate the installation process in that these can be removed/retracted easily when the DC is being loaded, and/or installed over the DC to support the load during the operational phase of pressure testing and operation. In some embodiments, the flexible material and/or straps may incorporate a heat transfer function such as by including heat transfer fluid channels or the like within the material thereof. In some embodiments, the support may be built into the DC material, such as between layers of DC material. For instance, one or more materials having greater resistance to pressure than the DC material (e.g., membrane) can be inserted or intertwined between two layers of material that together form the top section of the DC. In some embodiments, the inclusion of such a flexible material cover and/or multiple straps upon or within that top surface provides sufficient support such that fluid transfer to, e.g., another vessel or container) can be carried out without using equipment that is traditionally used with DCs (e.g., a peristaltic pump). In such embodiments, a gas may be introduced into the headspace thereby raising the pressure therein and facilitating fluid transfer. The pressure differential between the vessels controls the rate of liquid transfer. The higher the pressure in the supplying vessel (e.g., the DC) the faster the rate of transfer, assuming the receiving vessel is at atmospheric pressure and the liquid level in the supplying vessel is above the receiving vessel. There is no low limit on pressure as long as it is above atmosphere, and the upper limit is determined by vessel design and how the DC is supported. In some embodiments, then, fluid in the DC (e.g., "below" the headspace within the DC) can thereby be "pushed" out an open port and into another container (e.g., the fluid may be moved from the DC (e.g., bioreactor) and into a harvesting vessel). Thus, in some embodiments, the systems described herein comprise a disposable reaction container comprising an upper surface adjacent to the second zone comprising a headspace, and a flexible cover and/or straps adjacent to and/or incorporated into the upper surface. In some embodiments, the flexible cover and/or straps comprise at least one heat transfer fluid channel. In some preferred embodiments, the flexible cover and/or straps maintain the pressure upon the top surface of the DC at more than about 0.1-0.2 pounds per square inch (PSI). Accordingly, beyond the heat transfer function, the jacketed tank head, flexible material cover, and/or straps provide additional capabilities, safety and cost advantages to the system.

The reaction vessels described herein are typically, but not necessarily, constructed of metal and usually, but not necessarily, from a corrosion-resistant alloy. For instance, suitable materials may include, without limitation, sheet/plate stock (and/or dimple-jacket material for, e.g., heat transfer systems). Suitable exemplary materials include, for example, carbon steel, stainless steel (e.g., 304, 304L, 316, 316L, 317, 317L, AL6XN), aluminum, Inconel® (e.g., Inconel 625, Chronin 625, Altemp 625, Haynes 625, Nickelvac 625 and Nicrofer 6020), Incoloy®, Hastelloy (e.g., A, B, B2, B3, B142T, Hybrid-BC1, C, C4, C22, C22HS, C2000, C263, C276, D, G, G2, G3, G30, G50, H9M, N, R235, S, W, X), and Monel®, titanium, Carpenter 20®, among others. It is understood, however, that other materials besides or in addition to a corrosion-resistant alloy such as, but without limitation, plastic, rubber, and mixtures of such materials may also be suitable. A "mixture" of materials may refer to either an actual mixture per se to form a combined material or the use of various materials within the system (e.g., an alloy reactor shell and rubber baffle components).

A DC is typically comprised of a flexible material that is rigid and water impermeable such that a reaction may be carried out within without the DC losing its integrity, and the DC can be disposed of (e.g., removed from the reaction vessel) after use. The DC is physically supported by the reaction vessel and/or associated components, and typically includes and/or is attached to components allowing for attachment of it to the reaction vessel. The DC is also sealable so that sterile processes may be carried out within the same such that, e.g., failure is not caused by hydraulic forces applied thereto when it is filled with fluid. In some embodiments, the DC may be comprised of a flexible, water impermeable material such as a low-density polyethylene having a thickness in a range between about 0.1 mm to about 5 mm, or other appropriate thickness. The material may be arranged as a single or in multiple layers (e.g., single- or dual-ply). Where a DC comprises multiple layers, it may be comprised of two or more separate layers secured together by, e.g., an adhesive. Exemplary materials and arrangements that may be used include but are not limited to those described in U.S. Pat. Nos. 4,254,169; 4,284,674; 4,397,916; 4,647,483; 4,917,925; 5,004,647; and/or 6,083,587; and/or U.S. Pat. Pub. No. US 2002-0131654 A1. The disposable reaction container may be manufactured to have any desired size (e.g., 10 liters, 30 liters, 100 liters, 250 liters, 500 liters, 750 liters, 1,000 liters, 1,500 liters, 3,000 liters, 5,000 liters, 10,000 liters or other desired volumes).

The parts of the system (e.g., HS, optional additional coalescing unit, optional further condensing unit, and/or sterile filter) may be connected to one another by welding or other similar processes, or using a flexible material such as tubing (e.g., of a type standard in the industry). Those of ordinary skill in the art would understand such connection techniques.

The reaction container systems described herein comprise a zone (the second zone) providing a headspace (HS) formed within the container (e.g., a DC) that is continuous with and positioned above (relative to the flow of gas into and out of the system) the first zone in which a reaction is carried out (i.e., the first zone comprises the reaction mixture). The second zone (HS) provides a lower temperature than that present in the first (e.g., that of the reaction mixture). The lower temperature may be provided passively, e.g., by virtue of the temperature of the air surrounding the the DC or HS, but is more typically provided actively using, e.g., a heat exchange apparatus or heat transfer system. The heat transfer systems described herein may be constructed of any material through which heat transfer fluid (e.g., gas and/or liquid) may be transported such that heat may be conducted to and/or absorbed from another part of the system by radiative, convective, conductive or direct contact. In some embodiments, the heat transfer system may provide a fluidic pathway such as a channel through which heat transfer fluid can flow and/or circulate. The heat transfer systems may be composed of any suitable material, such as e.g., a dimple-jacket material.

The systems (e.g. reaction systems) described herein provide a reaction container with a first zone comprising a reaction mixture (e.g., an active fermentation reaction) being at or maintained at a high temperature (e.g., 37° C.); and a second zone (i.e., the HS), which typically comprises only humid gas and condensed fluid during use, at or maintained at a lower temperature than the first zone (e.g., perhaps only slightly lower such as 34° C. but in some embodiments at least about 5° C. lower). The reaction container may provide continuous surface along the walls, or it may be separated according to the dimensions of the first and second zones. The reaction container may also be constructed to only contain the first zone, while a separate apparatus is constructed to contain the second zone (e.g., is physically associated with the second zone) (e.g., the combination of heat transfer tubing and insulating material described herein). In some embodiments, the first and/or second zone (HS) are associated with a heat transfer system (HTS) which may be the same or different between the zones. In some embodiments, the temperature difference between the first and second zones may be maintained without associating a heat transfer system with the second zone. In some embodiments, however, the first and second zones (HS) are each associated with the same and/or different heat transfer systems. In some embodiments, the heat transfer system(s) may be what is commonly understood in the art to be "jacket" (e.g., a dimple-jacket material) through which a heat transfer fluid is circulated to provide for the transfer of heat between the first and/or second zones and the heat transfer system(s). In some embodiments, the first and/or second zones may be in contact with (e.g., at least partially surrounded by), the one or more heat transfer systems. In some embodiments, the first and/or second zones may be associated with more than one heat transfer system. For instance, in some embodiments, the second zone may be in contact with more than one jacketed heat transfer system including, for instance, the aforementioned jacketed tank head. In some embodiments, multiple sets of heat transfer baffles may be included (e.g., one or multiple types and/or arrangements in the first zone and another type or multiple types and/or arrangements in the second zone).

In some embodiments, the heat exchange apparatus may include one or more of the devices taught in any of, for instance, U.S. Pat. No. 2,973,944 (Etter, et al.), U.S. Pat. No. 3,986,934 (Muller, H.), U.S. Pat. No. 4,670,397 (Wegner, et al.), U.S. Pat. No. 4,985,208 (Sugawara, et al.), U.S. Pat. No. 4,460,278 (Tetsuyuki, et al.), a Platecoil® system, and/or heat transfer baffles such as, for example, that described in U.S. Pat. No. 8,658,419 B2 (Knight, C.; ABEC, Inc.) In some embodiments, the one or more heat transfer systems may comprise, for instance, as described in U.S. Pat. No. 8,658,419 B2, a first sub-assembly consisting essentially of a first material adjoined to a second material to form a first distribution channel; a second sub-assembly consisting essentially of a first material adjoined to a second material to form a second distribution channel; optionally a closure bar that adjoins the first assembly and the second sub-assembly to one another; and, a relief channel between the first sub-assembly and the second sub-assembly; wherein the closure bar, when present, sets the width of the relief channel, and, the distribution channels and the relief channel do not communicate unless a leak forms within a distribution channel. In some embodiments, such a heat transfer baffle may comprise two or more distinct compartments through which heat transfer media may be circulated independently of any other compartment. In some embodiments, such a heat transfer baffle(s) may be adjoined to the interior surface of a reaction vessel, wherein each baffle is adjoined to at least one heat transfer media inlet header and at least one heat transfer media outlet header, and the relief channel of each baffle is vented to the vessel exterior. In some embodiments, the heat transfer baffle(s) may be fixably attached to the interior surface of the reaction vessel at an angle relative to the interior wall or radius of the vessel, the angle being selected from the group consisting of about 5°, 10°, 15°, 20°, 25°, 30°, 35°, 40°, 45°, 50°, 55°, 60°, 65°, 70°, 75°, 80°, 85°, and 90°.

As mentioned above, in some embodiments, the one or more heat exchange systems may comprise jacket through which a heat transfer fluid is circulated. The jacket may, for instance, comprises channels through which the heat transfer fluid is circulated. In some embodiments, the jacket may be a "dimpled" material. Dimple jackets are typically installed around reaction vessels such as fermentation tanks and may be used as part of a heat transfer system. Dimple jacket material may be used in the devices described herein in the typical fashion, e.g., wrapped around the reaction vessel. In certain embodiments described herein, dimple jacket material may be also or alternatively used within the baffle structure. Dimple jacket materials are commercially available, and any of such materials may be suitable for use as disclosed here. Typically, dimple jacket materials have a substantially uniform pattern of dimples (e.g., depressions, indentations) pressed or formed into a parent material (e.g., a sheet of metal). Dimple jacket materials may be made mechanically ("mechanical dimple jacket") or by inflation (e.g., inflated resistance spot welding (RSW)), for example. To prepare a mechanical dimple material, a sheet of metal having a substantially uniform array of dimples pressed into, where each dimple typically contains a center hole, is welded to the parent metal through the center hole. An inflated RSW dimple material (e.g., inflated HTS or H.T.S.) is typically made by resistance spot welding an array of spots on a thin sheet of metal to a more substantial (e.g., thicker) base material (e.g., metal). The edges of the combined material are sealed by welding and the interior is inflated under high pressure until the thin material forms a pattern of dimples. Mechanical dimple materials, when used as jackets, typically have high pressure ratings and low to moderate pressure drop, while RSW dimple jackets typically exhibit moderate pressure ratings and a high to moderate pressure drop. Heat transfer fluid typically flows between the sheets of dimpled material. Other suitable dimple materials are available to those of skill in the art and would be suitable for use as described herein.

In some embodiments, the heat transfer system (e.g., one or more baffles and/or jackets) may be present across both the first and second zones (e.g., contacting both the reaction mixture and the HS). In such embodiments, the heat transfer system may provide for the cooling of the reaction mixture to a first temperature (e.g., 35-40° C. such as 37° C.) and the HS to a second temperature lower than the first temperature (e.g., 5° C. or more lower). In some embodiments, such a heat transfer system may only be associated with the first zone or only the second zone (i.e., the HS). In embodiments in which the heat transfer system is only present in the first zone, it serves to maintain the reaction mixture present therein to a first temperature. In such embodiments, the second zone (HS) may be maintained at a second temperature lower than the first temperature with or without using a heat exchange system. In some embodiments, the second zone (HS) may be maintained at a second temperature lower than the first temperature using heat transfer system such as a baffle(s) and/or a jacket(s) separate and distinct from that or those present in the first zone. In some embodiments, the separate and distinct heat transfer systems (e.g., baffle(s) and/or jacket(s) and/or fluidic channel(s)/tubing) may circulate the same or different heat transfer fluids, which may be maintained at the same or different temperatures. For instance, the heat transfer fluid circulating through the heat transfer system (e.g., baffle(s) and/or jacket(s)) present in the first zone may be maintained at a first heat transfer fluid temperature that is warmer or cooler than that circulating through the heat transfer system present in the second zone (HS).

In some embodiments, the second zone (headspace) may be at least partially surrounded by and directly contacting a heat transfer system such as one or more fluidic channels (e.g., a single piece of tubing, or multiple pieces of tubing) through which heat transfer fluid is circulated. The one or more fluidic channels are also connected to a source of heat transfer fluid by a suitable material (e.g., tubing). In some such embodiments, the reaction vessel may only provide physical support for the DC and/or the fluidic channel and not actually contain the fluidic channel (e.g., the fluidic channel is not positioned within the wall of the reaction vessel). In some embodiments, the fluidic channel may be comprised of a single or multiple channel(s) (e.g., tube having suitable heat transfer capabilities) that wraps around the second zone with spacing between channels varying as desired by the user. In some embodiments, the spacing is constant between each successive level of fluidic channel (e.g., as a fluidic channel transverses horizontally across and from the bottom toward the top of the second zone) and, in others, the spacing is variable between each successive level. In some embodiments, the spacing may be constant in certain sections of the second zone and variable in other sections of the second zone. In some embodiments, the one or more fluidic channels may be oriented essentially vertically (i.e., extending from the bottom of the second zone (i.e., closest to the top of the first zone) toward the top of the second zone). In some embodiments, fluidic channels may be positioned essentially horizontally as well as essentially vertically. Thus, in some embodiments, certain portions of the second zone will not be in direct contact with a fluidic channel and, in other embodiments, all or substantially all (i.e., 90% or more) of the the second zone will be in direct contact with the one or more fluidic channels. In some embodiments, the fluidic channel may directly contact the second zone (headspace) on one side and an insulating material on the other (i.e., that side of the fluidic channel further from the DC surface). In some such embodiments, the reaction vessel may enclose the first zone but not the second zone. In some embodiments, the one or more fluidic channels may be tubular in shape and comprised suitable heat-conducting material such as, but not limited to, copper. In some such embodiments, the coalescer may also be in direct contact with the one or more fluidic channels, and/or positioned upon the insulating material covering the fluidic channel but through which heat transfer to the coalescer may still be accomplished, above the second zone (see, e.g., coalescer 1 shown in FIG. 5). Other arrangements may also be suitable as would be understood by those of ordinary skill in the art.

Exemplary heat transfer fluids include but are not limited to one or more gasses and/or liquids. Suitable exemplary fluids and gases may include but are not limited to steam (top to bottom), hot and cold water, glycol, heat transfer oils, refrigerants, or other pumpable fluid having a desired operational temperature range. It is also possible to use multiple types of heat transfer media such that, for instance, one type of media is directed to one area of the reaction vessel and another type of media is directed to a different area of the reaction vessel (e.g., as in the zonal system described above). Mixtures of heat transfer media (e.g., 30% glycol) may also be desirable.

As mentioned above, the systems described herein comprise one or more coalescers for collecting fluid condensed in and escaping from (e.g., moving or migrating from) the headspace (HS) (i.e., the second zone). The function of the one or more coalescers is typically primarily to channel (or coalesce) smaller fluid droplets into larger fluid droplets. The gas entering the first zone (e.g., through the sparge) is typically a dry gas which becomes a humid gas (or a vapor, understood by those of ordinary skill in the art to be the gas state of a substance coexisting with its liquid) as it moves through the reaction mixture in the first zone. The gas exiting the first zone and entering the second zone (HS) is therefore a fully saturated humidified gas (i.e., this humidified gas, or vapor, has relative humidity of 100% ("fully saturated"); "relative humidity" being defined as a relationship between the actual weight or pressure (content) of water in air at a specific temperature and the maximum weight or pressure (capacity) of water that air can hold at that specific temperature; as compared to "absolute humidity", defined here as the amount of water vapor present in a gas mixture, measured as milligrams of water vapor per liter of air (mg/L ("water vapor content")). In this fully saturated state, cooling causes the humidified gas to transition into the liquid state (i.e., condense). Thus, the cooler temperature provided by the second zone (HS) condenses the humidified gas into its liquid form. At least some, and in most cases most (i.e., 50, 60, 70, or 80% or more), substantially all (i.e., 90% or more), or all, of the remaining humidified gas will then pass into the coalescer. Since the coalescer is at least partially on (e.g., in contact with) the jacketed tank head that provides heat transfer into the second zone (HS), the temperature within the coalescer will typically be higher than that in the second zone (HS) but is also still typically cooler than that provided by the first zone (i.e., it may be between that of the first and second zones). Thus, some condensation may occur in the coalescer. The primary benefit of the coalescer, however, is to provide increased residency time for the humidified gas as it travels from the disposable reaction container and out into the environment (e.g., through the exhaust vent), and for the collection any additional fluid formed from the humidified gas as it migrated through and from the second zone (HS). The gas exiting the coalescer and entering the filter therefore remains a humidified gas. Stated another way, the humidified gas is not dehumidified in either the second zone (HS) or the coalescer; any fluid collected simply represents a change in state from humidified gas to liquid. Given that some of the humidified gas exiting the first zone, entering and condensing in the second zone, some of which then enters the coalescer, is collected as fluid, a lesser volume of gas (i.e., the humidified gas) is processed through the filter. The increased residence time provided by the coalescer allows more of the gas that has transitioned into its liquid form to be collected therein prior to encountering the filter. It is noted as well that the filter is typically heated which provides for dehumidification of the gas. The gas which exits the filter and is exhausted into the environment is, therefore, a dehumidified gas.

Figure 1B:
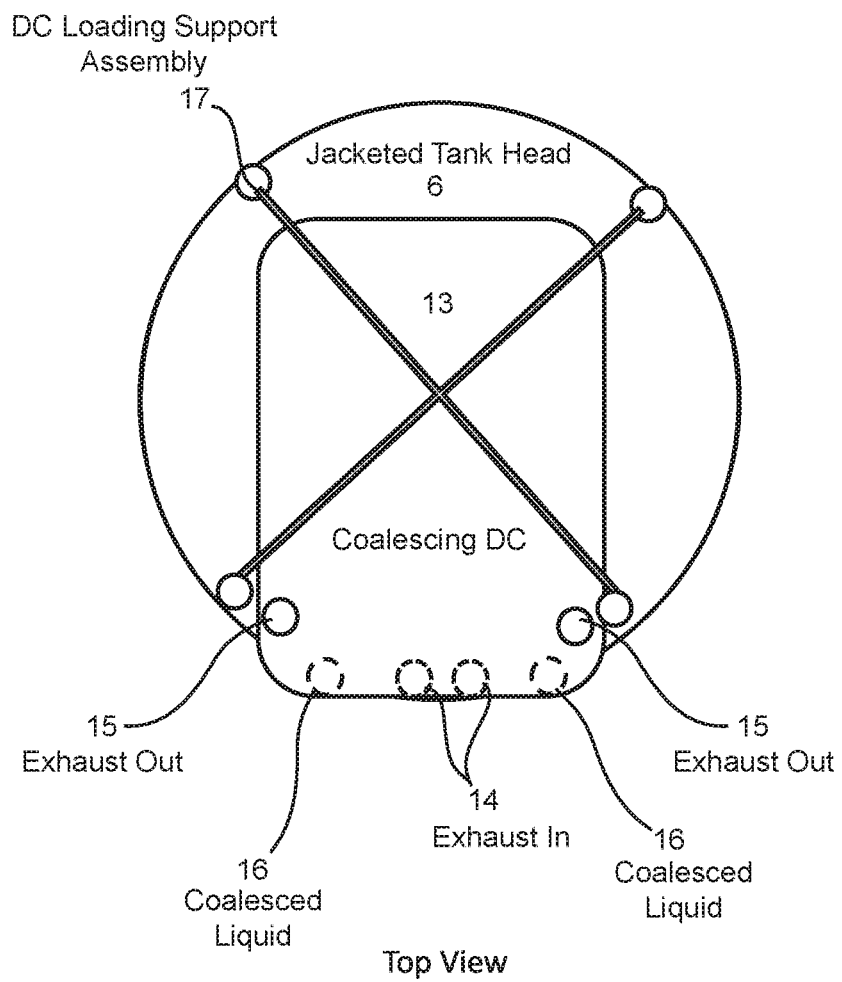
FIG. 1B provides a top view of an exemplary system.
Figure 1C:
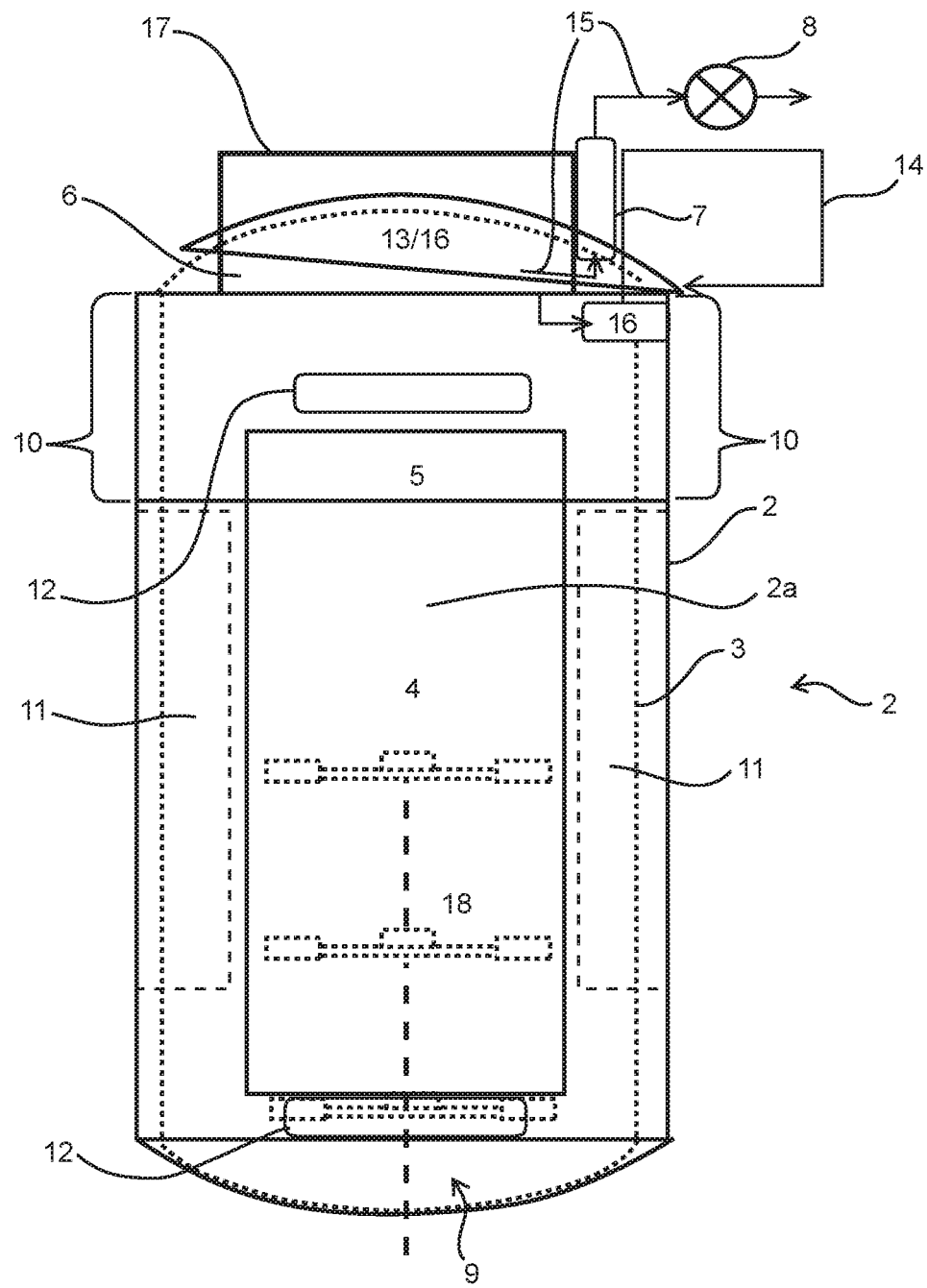
FIG. 1C provides a side view of another exemplary system.
Figure 1D:
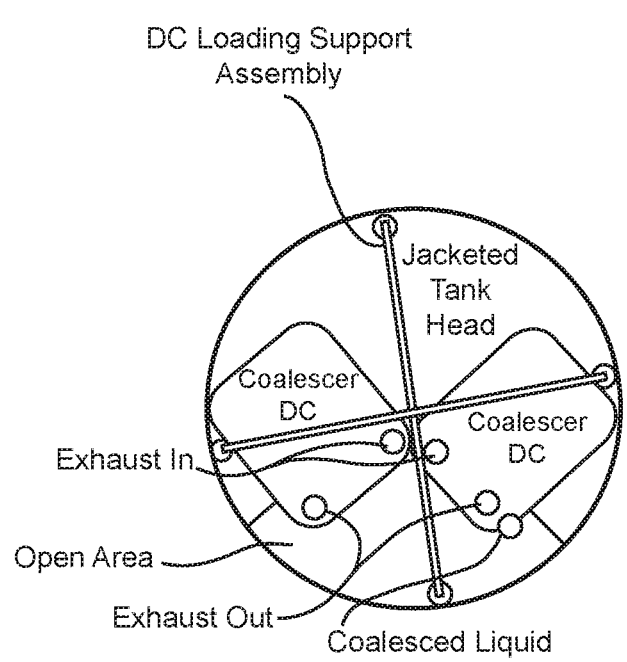
FIG. 1D provides a top view of an exemplary system comprising multiple coalescers.
Figure 5:
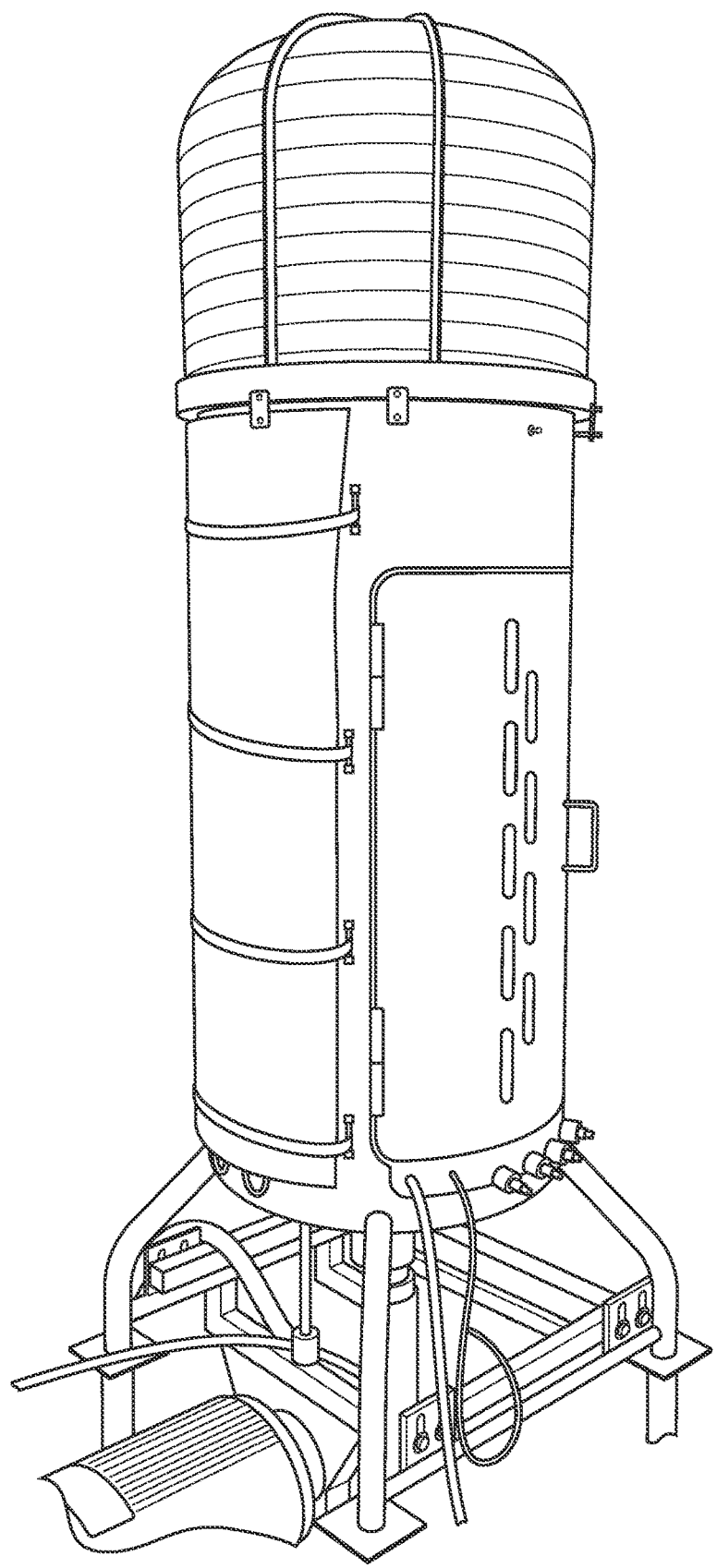
FIG. 5. Coalescer and associated tubing connecting coalesce and headspace (second zone) (1); headspace (second zone) surrounded by fluidic channel providing heat transfer, and insulating material (2); first zone with supply tubing and ports at bottom end (3).

The one or more coalescer(s) is/are typically positioned on top of the reaction vessel such as on top of the jacketed tank head (see, e.g., FIG. 1B, FIG. 1D, FIG. 5). Typically, but not necessarily, the one or more coalescers do not provide significant heat exchange and/or condensation. Heat exchange across the top of the headspace (second zone 5) is typically primarily provided by the jacketed tank head. In some embodiments, the jacketed tank head may provide heat transfer to the one or more coalescers since the same are positioned upon the jacketed tank head. The one or more coalescers may comprise an upper and a lower surface. The lower surface of each coalescer contacts (is on) the jacketed tank head, typically over some (e.g., at least about 10, 20, 25%, or more) of the surface area of the lower surface of the coalescer. In some embodiments, the lower surface of each coalescer contacts the jacketed tank head over at least about any of 5, 10, 15, 20, 25, 30, 35, 40, 45, 50, 55, 60, 65, 70, 75, 80, 85, 90, 95, or up to 100% of its surface area.

The one or more coalescers typically comprise tortuous and/or sinusoidal fluidic pathway (a "fluidic pathway" being an area through which a fluid may move) extending throughout or substantially throughout, e.g., greater than 50% of the interior portion of, the coalescer. In some embodiments, the one or more coalescers may comprise or may be a container (e.g., a flexible container) comprising one or more fluid channel(s) providing, e.g., a tortuous and/or sinusoidal fluid pathway within the coalescer. As described above, this tortuous and/or sinusoidal fluid pathway provides for increased residence time of the humidifed gas and increased collection of fluid. In some embodiments, the coalescer may be a flexible bag composed (or made) of a material suitable for use in a DC (e.g., a sterilizable, flexible water impermeable material such as a low-density polyethylene or the like, having a suitable thickness such as, e.g., between about 0.1 to 5 mm (e.g., 0.2 mm)). In some such embodiments, the coalescer may be produced by fusing at least two sheets of such flexible material together to provide an interior volume using standard techniques in the art. The turns of the tortuous and/or sinusoidal fluid pathway may be provided within that interior volume using similar techniques, e.g., fusing the flexible sheets together in a manner that provides a continuous fluidic pathway (e.g., channel) within the interior chamber thereof. In some embodiments, one or more of the coalescers may provide or may be a flexible, semi-rigid, or rigid tubular pathway (e.g., a tube) providing for cyclonic removal of gas from the headspace.

In some embodiments, the coalescer may also comprise, or be connected and/or attached to a device comprising mesh and/or packed solids (e.g., an "anti-foaming device", as described in US Pat. Pub. No. 2016-0272931 A1 (Rudolph, et al.)) Such a device may be positioned, e.g., between the DC and the one or more coalescer(s) such that humidified gas passes through the anti-foaming device before entering the one or more coalescers, between coalescers, within a coalescer, or between a coalescer and any other part of the systems described herein (e.g., a filter). In some embodiments, and as described in US Pat. Pub. No. 2016-0272931 A1, the anti-foaming device may comprise a container, the interior volume of which may include static mixer and/or granules (e.g., tortuous path) that collapse the foam (e.g., in the form of bubbles) that enters the anti-foaming device. The anti-foaming device typically includes an inlet receiving surface and a venting surface positioned opposite one another on either side of the chamber. The tortuous pathway is found within the chamber between the inlet surface and the venting surface of the anti-foaming device. The chamber may be in the form of tubing (e.g., plastic tubing), for example. Each of the gas inlet surface and the venting surface may be comprised of a material (e.g., a porous and/or mesh material) which serves to retain the granules. The material comprising the surfaces of the same may thus serve to compartmentalize the granules, thereby forming a container. In some embodiments, the anti-foaming device may be contained within a portion of tubing connected to the DC between the exhaust port at the top of the DC and before the exhaust. In such embodiments, the anti-foaming device does not necessarily need to form a completely separate piece of equipment but may instead exist within a piece of tubing through which the humid gas and/or fluid migrates out of the second zone (HS). In such embodiments, the anti-foaming device may be formed by positioning the material at either ends of a section of tubing that contains a tortuous fluidic pathway. One piece of said material may be positioned within the tubing to be proximal to the DC and distal to the vent, and function as a gas stream receiving surface. Another piece of material may be positioned within the tubing to be proximal to the vent and distal to the DC, and function as a venting surface. The tortuous fluidic pathway is thereby positioned between the gas stream receiving surface and the venting surface. In some embodiments, the tortuous fluidic pathway, the tubing, the material, and/or the DC are composed of substantially the same material. Alternatively, the anti-foaming device may be manufactured and then inserted into the tubing, for instance. In some such embodiments, humid gas migrating from the second zone (HS) encounters the anti-foaming device before entering the coalescer (e.g., the anti-foaming device is positioned between the second zone (HS) and the coalescer, and provides a gas outlet). A system may comprise one or more than one of such devices, e.g., a single device attached to the single coalescer of the system, multiple devices attached to the one or each one of the coalescer(s) of the system, and/or single individual devices being attached to multiple and/or each of multiple coalescers of the system. In some embodiments, then, the system may comprise a DC comprising a second zone (HS) from which the humid gas migrates through this device and into the coalescer. Other embodiments may also be suitable, as would be understood by those of ordinary skill in the art.

As described above, the humid gas (e.g., vapor, mist) passes from second zone (HS) into the coalescer through one or more fluidic pathways (e.g., tubes) connecting second zone (HS) and the coalescer. In some embodiments, such fluidic pathways may comprise, e.g., screens and/or other additional features (e.g., tubes) such that the nominal cross-sectional area in which the gas travels (e.g., as exhaust) would not create a substantial pressure drop. These fluidic pathways may also be or comprise and/or be associated with one or more input and/or output ports.

Thus, the coalescers described herein typically comprise one or more fluidic pathways (e.g., channel(s)) providing, e.g., a tortuous and/or sinusoidal fluid pathway, extending throughout, or substantially throughout. The coalescer is also typically connected to one or more input port(s) (e.g., an exhaust input) and/or one or more output port(s) (e.g., an exhaust output). The humid gas (e.g., vapor and/or mist) can migrate into the coalescer from the second zone (headspace) through the one or more input port(s) (e.g., through the pathway such as tubing associated therewith), continue through the fluidic pathway(s) of the coalescer(s), and out through the one or more output port(s) (e.g., through the pathway such as tubing associated therewith) which may be arranged at various positions therein (e.g., to the exterior through an exhaust vent). As the humid gas migrates through the fluid pathway(s) of the coalescer, fluid can condense on the walls thereof (e.g., in embodiments wherein the temperature therein is lower than in the second zone), and in some embodiments then passively return to the DC (i.e., second zone) and into the reaction mixture. In some embodiments, fluid that has not condensed but only coalesced (or collected) within the coalescer can also passively return to the second zone (HS) and/or the first zone (e.g., being deposited into the reaction mixture).

Figure 6:
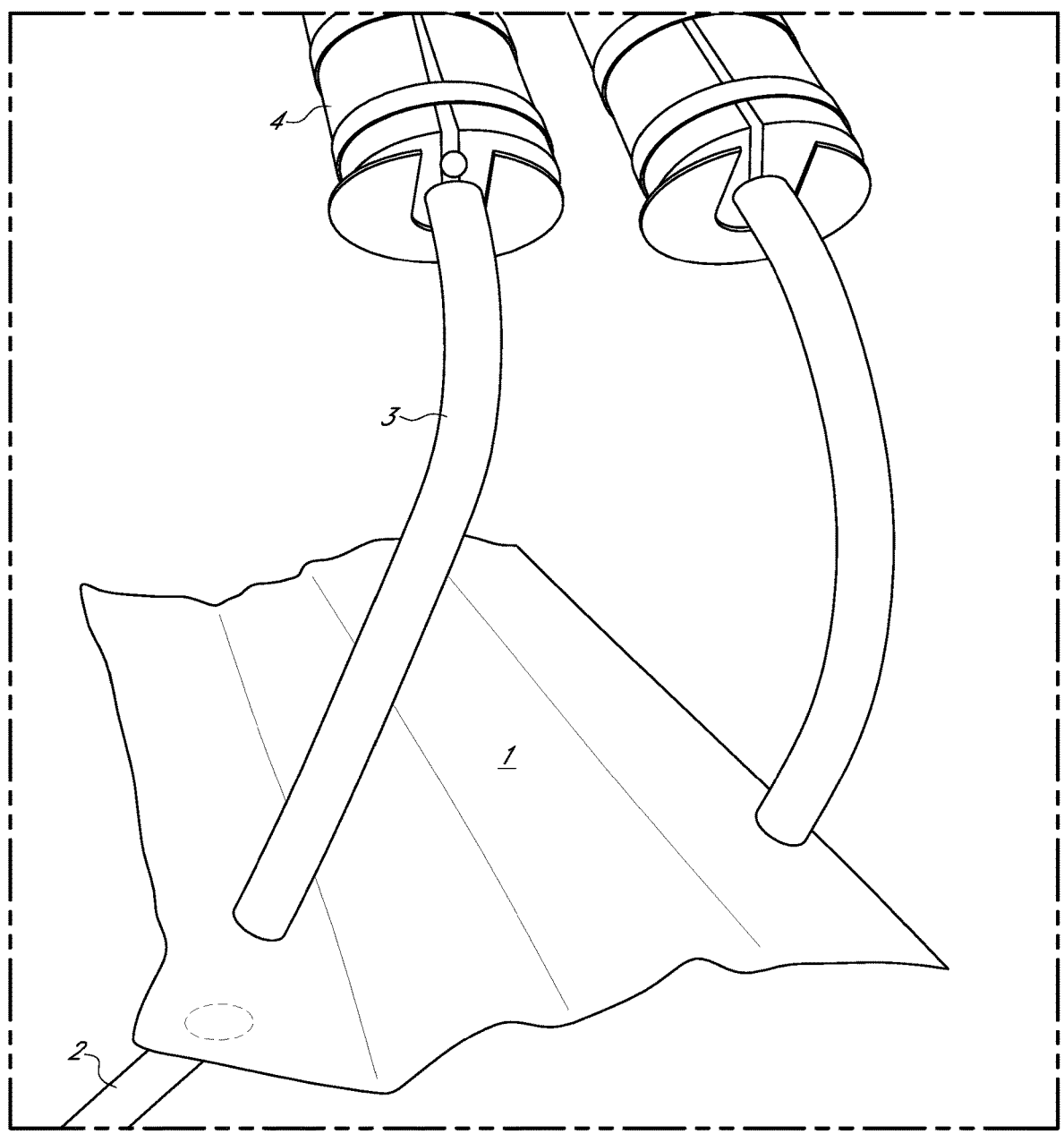
FIG. 6. Exemplary coalesce unit showing interconnected serpentine channels (1), intake tubing (2), exhaust tubing (3), and connected sterilizing filters (4).

In some embodiments, the coalescer may be arranged as a serpentine channel or multiple sets of substantially straight or straight main channels connected to one another through a connecting channel. Units of serpentine channels (e.g., at least one straight main channel or any two or more straight main channels connected by a connecting channel (e.g., 1 in FIG. 6), may be physically connected to one another but also may or may not allow fluid and/or gas to pass between such units. In some embodiments, one or more of said main channels are connected to one or more intake ports from the second zone (headspace) (e.g., connected by tubing at a main channel; e.g., 2 in FIG. 6). An exit/exhaust port through which non-coalesced fluid may pass to the exhaust system (e.g., the one or more filters (e.g., 4 in FIG. 6) is also positioned within said main channels, and is used to connect the same to the filter(s) via a suitable pathway (e.g., tubing (e.g., 3 in FIG. 6)). In some embodiments in which the coalescer is positioned horizontally or substantially horizontally on the reactor (e.g., upon the headspace, or insulation surrounding the headspace), the intake port is positioned closest to the second zone (headspace) (e.g., at the bottom of the main channel) and the exit port is positioned distal from the second zone (headspace) relative to the intake port (e.g., at the top of the main channel). Thus, the fluid moves from the second zone (headspace), through a connector (e.g., tubing) and into the coalescer where non-coalesced fluid migrates through the main channels (e.g., in some embodiments through one or more connector channels as well) to the exit pot and through a connector (e.g., tubing) connected to the exhaust system (e.g., a filter), and then exists the system into the atmosphere.

In some embodiments, multiple coalescers can be included in the system (as in, e.g., FIG. 1D). Such multiple coalescers may be connected to one another by one or more fluid channels (e.g., tubing) through, for example, the one or more input and output ports. In such embodiments, each coalescer may be connected to the DC individually and/or through one or another coalescer. Where multiple coalescers are included, only one, more than one, or all of the coalescers may be in contact with the jacketed tank head.

As mentioned above, one or more filters may be included in the system. The filter is of a type typically used in disposable reactor systems such as, but not necessarily, a sterile filter such as e.g., a 0.2 micron filter. The filter is typically connected (e.g., using tubing) to the HS and/or, more typically, the coalescer. To improve the function of the filter, one or more heating elements may also be associated therewith (e.g., contacting the external surface of the filter) and may serve to dehumidify saturated gas that has exited the coalescer. As discussed below, the exhaust system may include a vacuum pump for pulling air and/or gas from within the system to the exhaust system which may even further improve the useful life of the filter. Thus, the use of heat and/or a vacuum decreases the likelihood of fluid accumulating within, and thereby increasing the functionality of, the filter. Accordingly, one or more filters may be used in the systems described herein.

The system also typically includes an exhaust system. The exhaust system may comprise an exhaust pump such as a vacuum. In some embodiments, tubing may connects the exhaust pump downstream of a sterile barrier filter attached to the reaction container (e.g., DC); tubing connects the exhaust pump to the coalescer and an inlet or an outlet of a sterile barrier filter attached to the reaction container (e.g., DC); the exhaust pump comprises variable speed control and being optionally operably linked to instrumentation for maintaining reaction container (e.g., DC) pressure; a first fan, optionally located on the coalescer, draws exhaust gas from the headspace through the coalescing device and into or through a downstream sterile barrier; and/or, the system comprises at least a second fan recirculating exhaust gas within the condenser headspace and/or coalescing device. Each of such exhaust systems provides for the removal of air and/or gas (dry or moist) from the reaction container system. Exemplary exhaust pumps and exhaust systems may include but are not limited to those described in, for instance, US Pat. Pub. No. 2011/0207170 A1 (Niazi, et al.).

The systems described herein may also include one or more manual and/or automated control systems (e.g., not requiring continuous direct human intervention), including but not limited to one or more remotely controlled control systems. For instance, a control system may continuously monitor one or more conditions occurring within the first and/or second zones (e.g., temperature) and adjust the same to maintain a particular value (e.g., a closed loop system). Using temperature as an exemplary condition, the control system can separately monitor the temperature of the first zone, the second zone (headspace), and/or coalescer (e.g., by being connected to thermostats in each that independently report temperatures to the control system) to optimize the temperature of the reaction components in each area of the system. The temperature may be optimized by, for example, increasing or decreasing the temperature in these areas by modifying the type, temperature, and/or speed of the heat transfer fluid moving through the heat transfer system. Such a control system may be used to maintain the temperature of the first zone at, for instance about 37° C. and the temperature of the second zone (headspace) at a temperature of about 32° C. Such control systems typically comprise one or more general purpose computers including software for processing such information and manually or automatically adjusting the desired parameters of the reaction as required by a particular process. As such, the control system may control valves and the like controlling the flow of heat transfer materials to and from the system (e.g., the one or more heat transfer systems thereof).

An exemplary embodiment of a DC system described herein is illustrated in FIG. 1. FIG. 1A provides a front view of an exemplary DC system 1 including reaction vessel 2 (typically including door 2a) comprising within it disposable reaction container 3, first zone 4, second zone 5 (i.e., the headspace ("HS")), jacketed tank head 6 (illustrated in more detail in FIG. 1B, and which could be a third zone where a third heat transfer system is used here (e.g. "Zone 3" in FIG. 2)), filter 7, exhaust pump 8, air input (e.g., sparge) 9, heat exchange apparatus(es) 10 (e.g., heat exchange jacket surrounding second zone 5) and/or 11 (e.g., heat exchange baffle(s) 11 being positioned in first zone 4, such baffle(s) optionally extending into and/or also being positioned (e.g., as separate baffles with a heat transfer function independent from those in zone 4) in second zone 5), coalescer 13 contacting jacketed tank head 6, exhaust input 14, exhaust output 15, coalesced liquid 16, DC loading support assembly 17, and a drive system 18 (e.g., comprising impellers). Optional port belts (12) may also be included and positioned as needed and/or desired (e.g., as shown in FIG. 1A). Typically, non-aerated liquid is present in first zone 4 and aerated liquid is present in second zone 5 (HS) along with humid gas, although some non-aerated liquid may be present in second zone 5 (HS) (e.g., where the top level of the reaction mixture extends into zone 5 (HS)). The reactor vessel may also comprise a door through which the DC and/or other components of the system may be inserted and removed therefrom (2a, and see FIG. 2). The top view provided in FIG. 1B further illustrates jacketed tank head 6, coalescer 13 contacting (e.g., on) jacketed tank head 6 and comprising exhaust inputs 14, exhaust outputs 15, coalesced liquid 16, and DC loading support assembly 17. FIG. 1C provides a side view of this exemplary embodiment. As shown therein, in this embodiment, coalescer 13 covers approximately 75% of the top of second zone 5 (HS) and is contacting and/or positioned on jacketed tank head 6. DC 3 is positioned within reaction vessel 2 and provides a space (the first zone 4) within which a reaction takes place (e.g., a fermentation) and a headspace (the second zone 5).

Figure 1E:
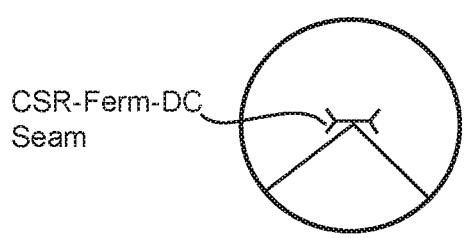
FIG. 1E provides top view of a system in which the jacketed tank head covers most of the top of a DC including a top seam thereof.
Figure 1F:
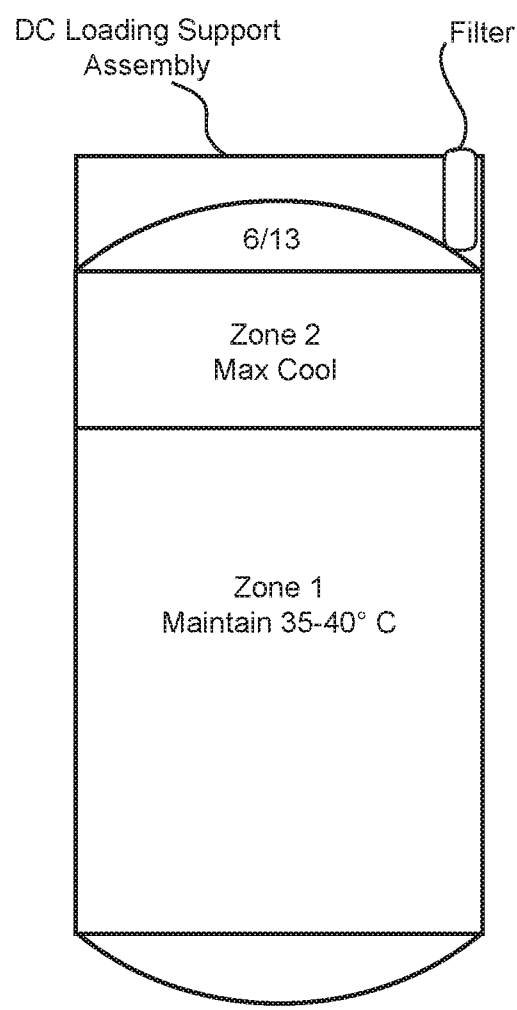
FIG. 1F provides another side view of a general layout of an exemplary system.

FIGS. 1D-F provide additional views of these and other embodiments. FIG. 1D provides a view of an embodiment in which multiple coalescers are positioned on the jacketed tank head. FIG. 1E provides a top-down view of the jacketed tank head covering approximately 75% of the top surface of the DC where, in this embodiment, the seam in the DC is covered by the jacketed tank head, thereby providing additional physical support thereto. FIG. 1F illustrates a side view of the DC in which the first zone ("Zone 1") is maintained at 35-40° C. and the second zone (HS) is maintained at a cooler temperature (designated "Max Cool" is this illustration).

As discussed above, and with reference to FIG. 1, disposable reaction container 3 comprises first zone 4 in which a reaction is carried out and second zone 5 providing a headspace (HS). First zone 4 therefore typically comprises a fluid reaction mixture (e.g., the components and products of a biological reaction) which may be agitated (e.g., stirred) by drive system 18 (e.g., comprising impellars). Air (e.g., gas) is typically introduced into first zone 4 and migrates into and/or through the reaction mixture. Second zone 5 (HS) typically extends from the top fluid level of the reaction mixture and the top of DC 3 (which typically extends to the top of reaction vessel 2 and/or and/or is physically supported by jacketed tank head 6). The first and second zones may also be associated with (e.g., in contact with) one or more heat exchange apparatus(es) 10 and 11 that may be the same or different in each zone. The heat exchange apparatus(es) may individually or together (e.g., when included a single unit transversing first zone 4 and second zone 5 (HS)) serve to maintain the average temperature of the reaction mixture contained within disposable reaction container 3, and more specifically first zone 4 and/or second zone 5 (HS). The heat exchange apparatus(es) are typically arranged to maintain a desired temperature in first zone 4 and a lower (i.e., cooler) temperature in second zone 5 (HS) in order to induce condensation in the HS. For instance, a heat exchange apparatus may maintain the temperature of first zone 4 at 35-40° C. and the temperature of second zone 5 (HS) at a temperature of, for instance 30° C. The heat transfer fluid of a single heat transfer apparatus extending between first zone 4 and second zone 5 may maintain the different temperatures of these zones since the temperature of the reaction mixture is typically higher than the temperature of the headspace. The cooling effect provided by the heat exchange apparatus can therefore be relative to the temperature of the contents of each zone (e.g., the reaction mixture within first zone 4 and the air and the like within second zone 5 (HS)). For instance, the temperature of a reaction mixture in first zone 4 may be lowered from 50° C. to 40° C. by the heat exchange apparatus, while the temperature within second zone 5 may be lowered from 35° C. to 30° C. by the same heat exchange apparatus. As mentioned above, in some embodiments, different heat exchange apparatuses may be provided to each of first zone 4 and second zone 5, and each of such apparatuses may separately cool their respective zones.

As described above, the heat exchange system may comprise a jacketed system (10) surrounding disposable reaction container 3, and/or one or more baffle systems (11). The jacketed system may be incorporated into the vessel as part of a vessel wall, for example. Jacketed tank head 6, positioned at the top end of the reaction vessel, may be jacketed as described herein (e.g., using a dimpled sandwich arrangement) and typically covers at least 5% of the top surface of second zone 5 (HS). In some embodiments, jacketed tank head 6 may cover more than 5% of the top surface of second zone 5 (HS), such as about any of 10%, 20%, 30%, 40%, 50%, 60%, 70%, 80%, or 90% of that surface. Associated with or positioned upon, or adjacent to or on, jacketed tank head 6 in the embodiment illustrated by FIG. 1, is coalescer 13. As mentioned above, at least one surface of the coalescer typically contacts jacketed tank head over part (e.g., at least about 25%) of the surface area of that coalescer surface. Coalescer 13 comprises exhaust input(s) 14 connected to second zone 5 (HS) through which gas moves from second zone 5 into coalescer 13, and exhaust output(s) 15 through which gas (e.g., humidified gas) may leave coalescer 13 and enter the exhaust system for discharge from the system (e.g., into the environment). Exhaust output 15 is typically also connected to filter 7, which is connected to exhaust system 8. Coalesced liquid 16 typically leaves second zone 5 (HS)

and collects in coalescer 13. Coalesced liquid 16 may or may not leave coalescer 13 but is typically not actively removed therefrom. As such, coalesced liquid 16 may leave coalescer 13, e.g., passively (e.g., by gravity) returning to second zone 5 (HS) and then, typically first zone 4. This movement is illustrated in FIG. 1A by the upward and downward pointing arrows positioned between second zone 5 and coalescer 13. In this embodiment, the various parts of the system including but not limited to second zone 5 (HS), coalescer 13, filter 7 and exhaust system 8 are connected using flexible tubing.

Figure 2A:
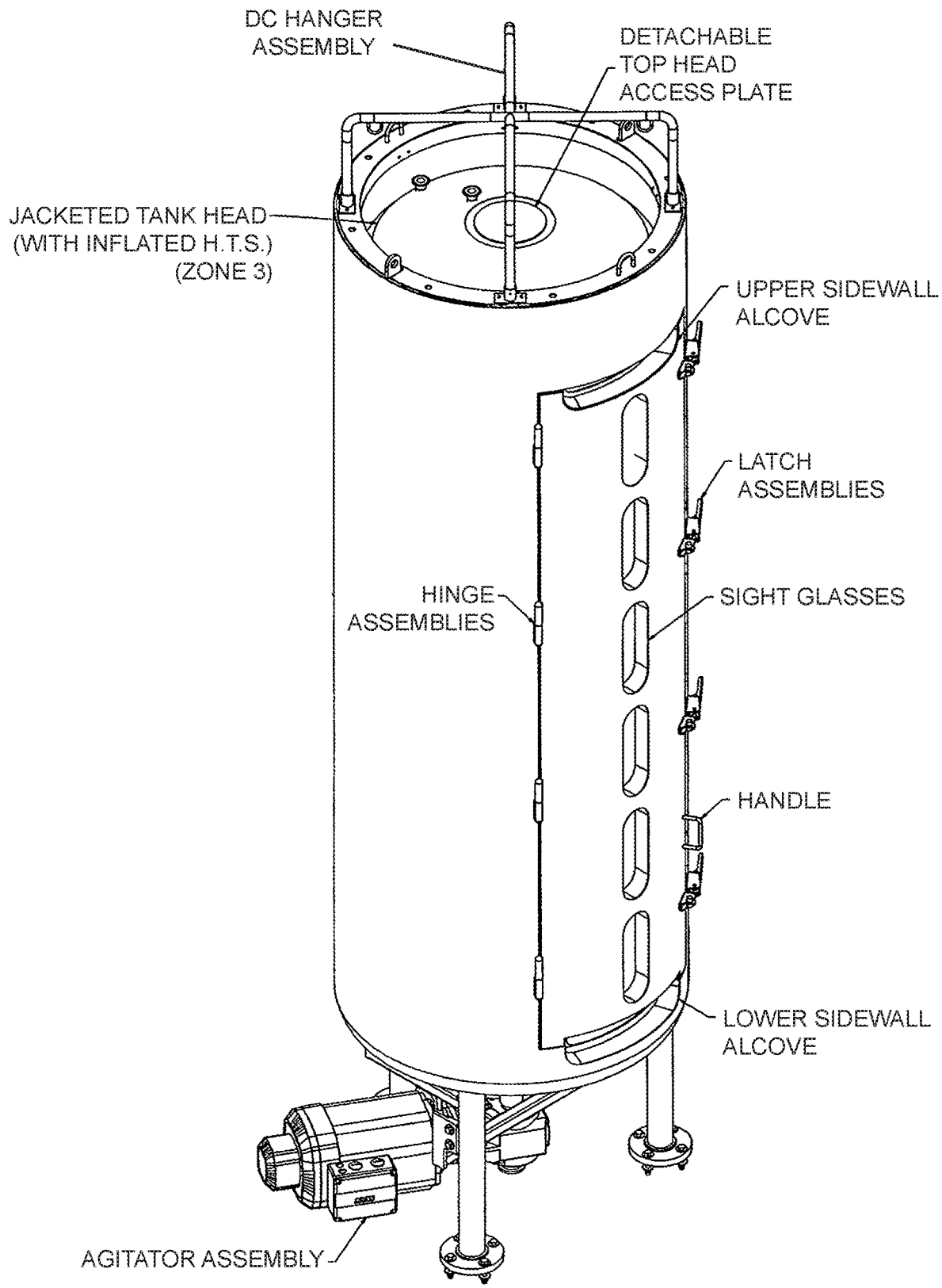
FIG. 2A provides a view of an exemplary reactor vessel.
Figure 2B:
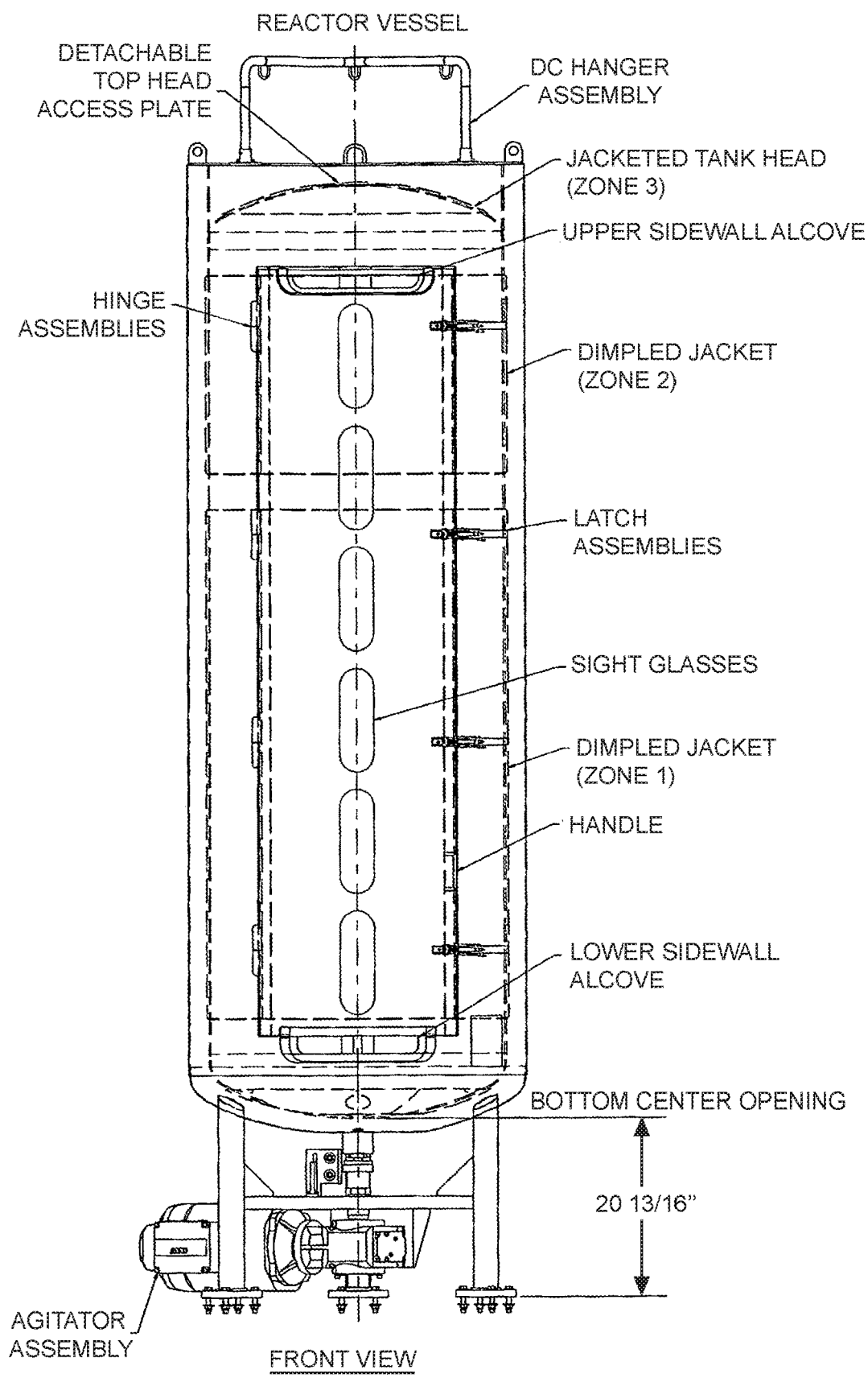
FIG. 2B provides yet another view of an exemplary reactor vessel.
Figure 2D:
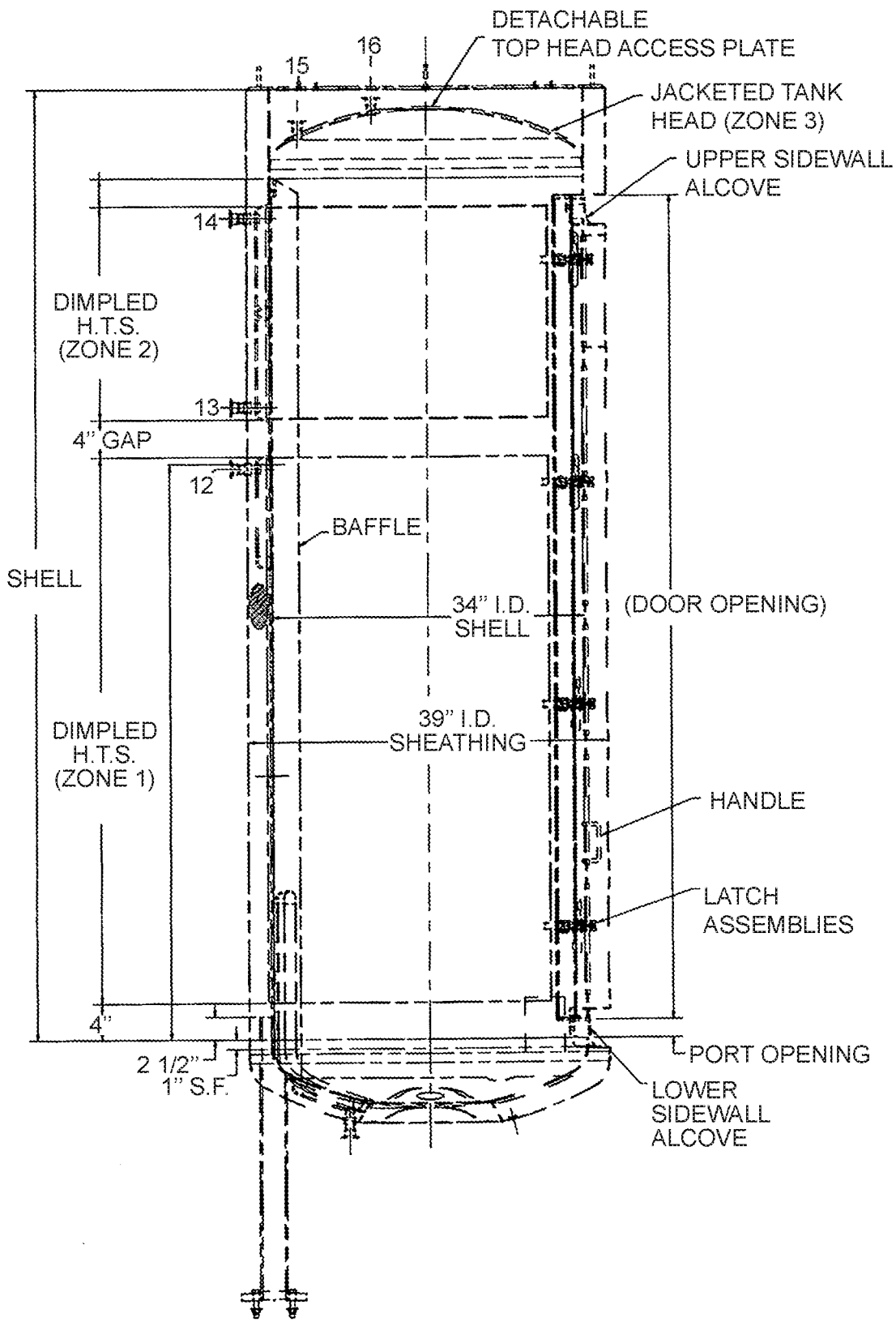
FIG. 2D provides a side view of an exemplary reactor vessel.
Figure 2E:
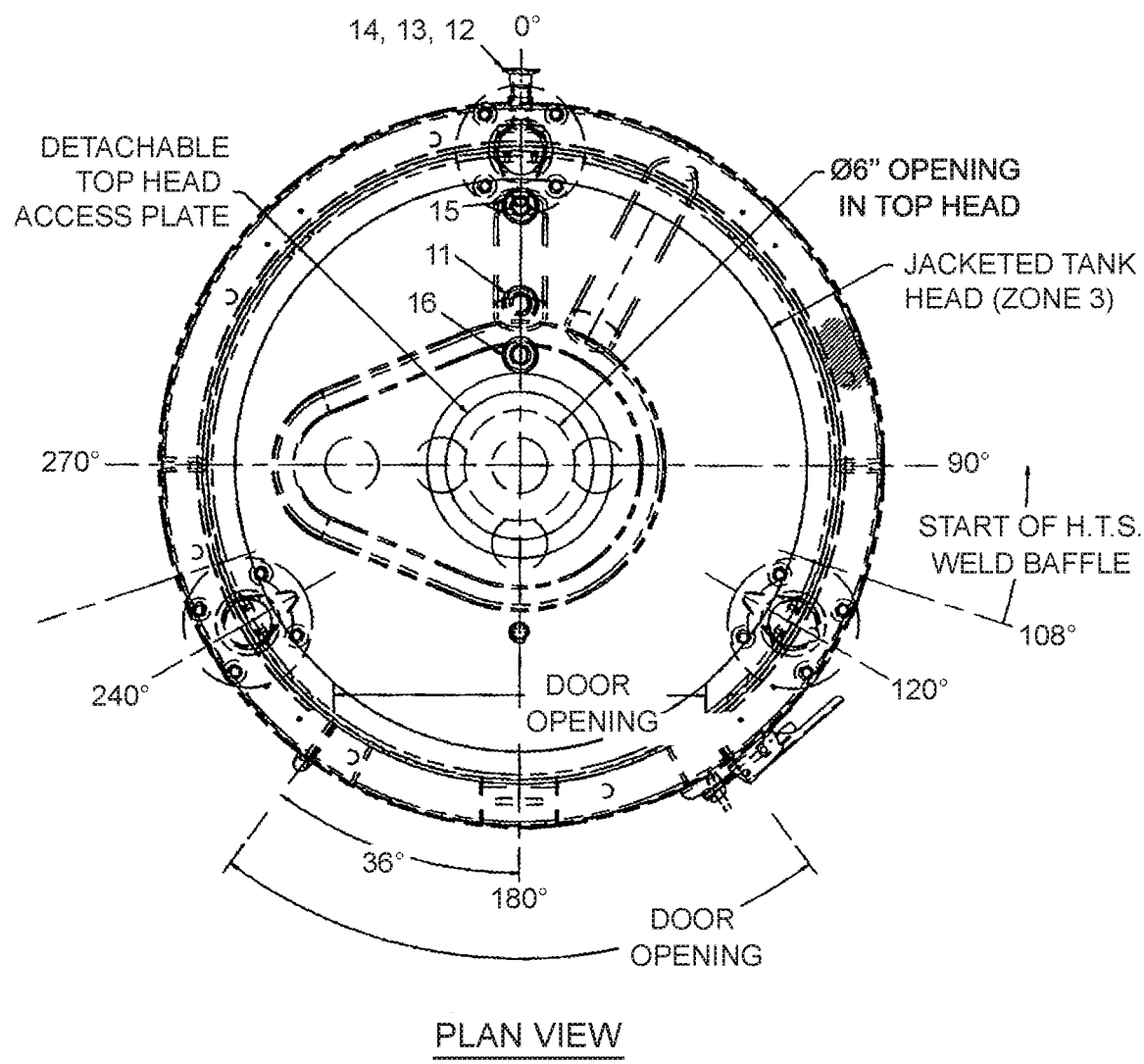
FIG. 2E provides an additional top view of an exemplary reactor vessel.

FIGS. 2A-E illustrate various views of an exemplary reactor vessel in which a DC may be maintained. As shown in FIG. 2A, for instance, the reactor vessel may comprise and agitator assembly, a door secured by hinge and latch assemblies, a top head with heat transfer capabilities (i.e., a dimpled jacket structure provided by "Jacketed Tank Head (with inflated heat transfer surface (H.T.S.)) (Zone 3)"), and DC loading support assembly. FIG. 2B provides another view of the reactor vessel, showing dimpled heat transfer surfaces associated with the first and second zones (e.g., "Dimpled Jacket (Zone 1)" providing heat transfer to first zone 4; and "Dimpled Jacket (Zone 2)" and Jacketed Tank Head ("Zone 3") providing heat transfer to the second zone 5 (HS), these heat transfer systems being contiguous or not contiguous with one another). FIG. 2C provides top view of this exemplary reactor vessel and another view of the jacketed tank head ("Jacketed Tank Head (Zone 3)") FIG. 2D illustrates a view of the reactor opposite that of FIG. 2A (i.e., the door is on the opposite side of the reactor vessel shown in this view), and also shows dimpled heat transfer surfaces associated with zones 1 and 2 ("Dimpled H.T.S. (Zone 1)" and "Dimpled H.T.S. (Zone 2)", respectively), as well as "Jacketed Tank Head (Zone 3)" also providing heat transfer to the second zone 5 (HS)). FIG. 2D also shows a "4" Gap" between the heat transfer surfaces of the first and second zones. It should be understood that the length of this gap may vary, and 4" is only referred to here as a non-limiting example. FIG. 2E also shows the "Jacketed Tank Head (Zone 3)", similar to FIG. 2C. It should be understood that each of these illustrations are only exemplary, and variations may be made thereto.

Figure 3:
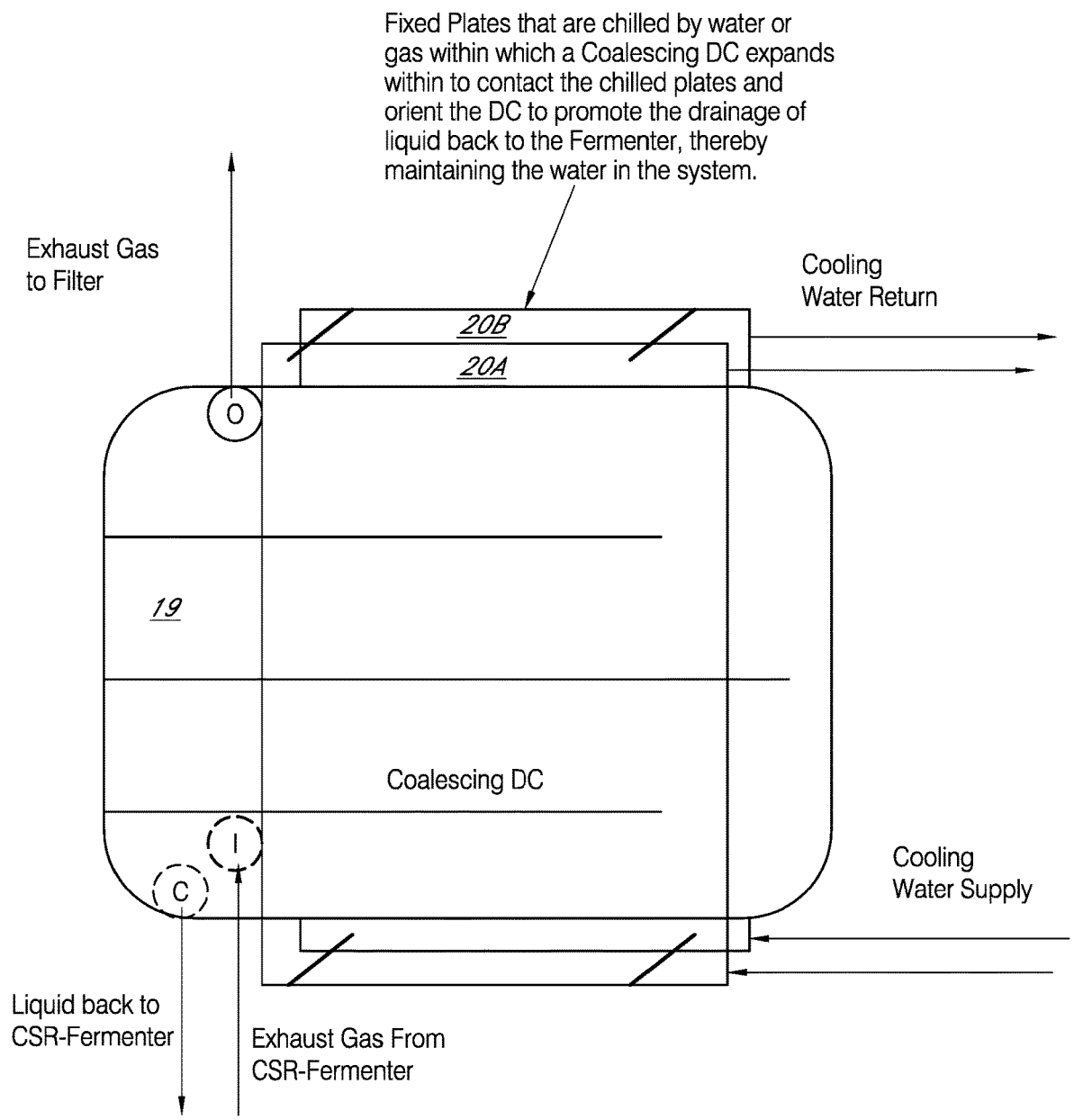
FIG. 3 illustrates yet another embodiment of a coalescer of the system.

FIG. 3 illustrates an alternate or additive arrangement of the system in which a coalescing device comprising a coalescer (19) is at least partially contacting and/or constrained by one or more heat transfer surfaces (e.g., one or more dimple jacket-type heat transfer units such as 20A and 20B) other than or in addition to the jacketed tank head is connected thereto. In such embodiments, one or more heat transfer surfaces chilled by a heat transfer fluid (e.g., water), such as one or more plates (preferably two positioned on either side of the coalescer) that contact the coalescer or come into contact with the coalescer as it expands as result of the entry of fluid (coalescate ("C")) and humidified gas into the coalescer (e.g., where the coalescer is constructed of a flexible material surrounding an interior chamber, including as tubing alone and/or contained within an interior chamber) through the gas intake thereof ("I"), and cool the interior chamber and its contents. In these embodiments, as in others described herein, the coalescer provides a tortuous and/or serpentine fluid pathway through which the coalescate and/or humid gas may migrate. The fluid pathway may also comprise one or more types of mesh and/or solids (like the anti-foam device described above) throughout all or part thereof. The surface area of the coalescer in these embodiments is typically not in contact with the heat transfer surfaces over its entire surface area. For instance, in some embodiments, the coalescer contacts the one or more heat transfer surfaces over 50% or less of its surface area (see, e.g., the example illustrated in FIG. 3). As in other embodiments, the contents of the coalescer may also be cooled by the ambient temperature of the environment surrounding the coalescer that are not in contact with the active heat transfer system (e.g., the one or more plates), the ambient temperature typically being about room temperature (e.g., 25° C.). The contents of the interior chamber are typically humidified gas and liquid migrating from the headspace (e.g., zone 5). Expansion of the coalescer promotes drainage of coalesced liquid back into the DC, either by passive forces (e.g., gravity) or actively (e.g., using a pump). Humidified gas continues its migration through the system, moving through the coalescer and out the exhaust thereof ("O"), then the filter (which may be heated to dehumidify the humidified gas), and into the environment through an exhaust outlet. Such movement may be assisted through the use of an exhaust system as described above which may comprise, e.g., one or more fans.

This disclosure provides and describes system(s) (e.g., reaction systems) comprising a reaction container (e.g., a DC); at least one heat transfer system; a jacketed tank head positioned above the reaction container (e.g., a DC); and, one or more coalescers comprising an internal tortuous fluidic pathway and contacting (e.g., typically being positioned on) the jacketed tank head; wherein: the disposable reaction container can comprise a first zone that can comprise a reaction mixture maintained at a first temperature; the disposable reaction container can comprise a second zone comprising a headspace above the reaction mixture into which humid gas migrating from the reaction mixture can migrate; the second zone can be maintained at a second temperature lower than that of the first temperature; and, fluid migrating from the second zone may coalesce within the internal tortuous fluidic pathway of the coalescer. In some embodiments, then, the system includes: at least one disposable reaction container comprising first and second zones, the first zone comprising a reaction mixture and the second zone comprising a headspace into which humid gas migrates from the first zone; at least one heat transfer system for maintaining the first zone at a first temperature; at least one heat transfer system for maintaining the second zone at a second temperature lower than the first temperature; and, fluid migrates from the headspace (i.e., the second zone) coalesces within the internal fluidic pathway of the coalescer. In some embodiments, the system comprises a reaction vessel comprising a heat transfer system. In some embodiments, the jacketed tank head is integral with the reaction vessel. In some embodiments, the reaction vessel also comprises one or more heat transfer baffles. In some embodiments, the jacketed tank head physically supports a disposable reaction container. In some embodiments, heat transfer is accomplished by radiative, convective, conductive or direct contact, and/or the heat transfer fluid is gas and/or liquid. In some embodiments, a first heat transfer system is associated with the first zone and a second heat transfer system is associated with the second zone. In some embodiments, a third heat transfer system is also provided by the jacketed tank head, and may be in fluidic communication with the first and/or second heat transfer systems. In some embodiments, at least two of the heat transfer systems are contiguous with one another (e.g., interconnected by a fluidic pathway), at least one of the heat transfer systems is not contiguous with at least one other heat transfer system. In some embodiments, the second and third heat transfer systems are interconnected. In some embodiments, the same type of heat transfer fluid is in each of the one or more of the heat transfer systems, while in some embodiments, the heat transfer fluid in each of the one or more heat transfer systems is different. In preferred embodiments, the second zone is positioned above the first zone, "above" being relative to the direction of flow of the humid gas from the reaction mixture in the first zone into the second zone (e.g., the second zone is physically above the first zone). In some embodiments, the second zone is partially defined by an upper exterior surface adjacent to the jacketed tank head. As mentioned above, this arrangement allows the disposable reaction container to withstand higher pressures than would otherwise be possible. In some embodiments, the or at least one of the coalescers comprises upper and lower surfaces and the internal tortuous fluidic pathway is contiguous with either of both of said upper and/or lower surfaces. In some embodiments, the or at least one of the coalescers is comprised of at least two pieces of flexible material fused together to form a chamber comprising the internal tortuous fluidic pathway. In some embodiments, the internal tortuous fluidic pathway of the can be defined by fused sections of the at least two pieces of flexible material. In some embodiments, the internal tortuous fluidic pathway is defined by a third material contained within the chamber. In some embodiments, at least one anti-foam device positioned between the disposable reaction container and the or at least one of the coalescers. In some embodiments, the system may comprise, typically configured as part of the reactor vessel, at least one baffle comprising a first sub-assembly consisting essentially of a first material adjoined to a second material to form a first distribution channel; a second sub-assembly consisting essentially of a first material adjoined to a second material to form a second distribution channel; optionally a closure bar that adjoins the first assembly and the second sub-assembly to one another; and, a relief channel between the first sub-assembly and the second sub-assembly; wherein the closure bar, when present, sets the width of the relief channel, and, the distribution channels and the relief channel do not communicate unless a leak forms within a distribution channel. In some embodiments, at least one such baffle is associated with the first zone and a separate such baffle is associated with the second zone. As mentioned above, in some embodiments, the system may comprise multiple coalescers that may or may not be interconnected through one or more fluidic pathways and/or at least one anti-foam device. In some embodiments, at least one or each coalescer comprises a lower surface and that at least about 25% of the surface area of said lower surface is on the jacketed tank head. In some embodiments, the coalescer can comprise a flexible container comprising a tortuous fluid pathway; a flexible, semi-rigid, or rigid tubular form providing for cyclonic removal of gas from the headspace; and/or, a container comprising mesh and/or packed solids. Typically, the systems described here comprise an exhaust pump. In some such embodiments, tubing can connect the exhaust pump downstream of a sterile barrier filter in fluidic communication with the disposable reaction container; tubing can connect the exhaust pump to the coalescer and an inlet or an outlet of a sterile barrier in fluidic communication with the disposable reaction container; the exhaust pump can include variable speed control and/or can optionally be operably linked to instrumentation for maintaining DC pressure; the exhaust system can include at least a first fan, optionally located on the condenser, that can draw exhaust gas from the headspace through the coalescing device and into and/or through a downstream sterile barrier; and/or, optionally at least one fan recirculating exhaust gas within the condenser headspace and/or coalescing device. In some embodiments, the system comprises a heat transfer system at least partially directly in direct contact with the exterior of the second zone and is at least partially not positioned within the reaction vessel (e.g., as illustrated in FIG. 5). Those of ordinary skill in the art will be able to derive additional embodiments from this disclosure.

In some embodiments, the systems described herein may comprise one or more pressure transmitters or sensors, load cells, and/or scales (e.g., platform scale) in contact with the second zone (e.g., headspace) which measures the pressure upon the walls of the reaction container within the second zone by, e.g., gases and fluids present therein. In some embodiments, the pressure transmitter can be a diaphragm pressure transmitter or load cell(s). The pressure transmitter may include a membrane for detecting pressure on the walls of the reaction container. In some embodiments, the pressure transmitter(s) or load cell(s) contact the exterior surface of the reaction container (e.g., the membrane of a diaphragm pressure transmitter contacts the exterior surface of the reaction container adjacent to the second zone). In some embodiments, the pressure transmitter is in communication with a control system for monitoring (e.g., continuously monitoring) the pressure within the second zone (e.g., by receiving and analyzing information regarding that pressure) and adjusting the same as required to ensure the pressure does not exceed the ability of the reaction container (e.g., the disposable reaction container) to maintain its integrity in the presence of that pressure. In some embodiments, the control system adjusts the pressure within the second zone using an exhaust pump (e.g., by activating the exhaust pump to remove some of the gases and the like from the second zone). In some embodiments, the control system is automated (e.g., using software). Other embodiments comprising such pressure transmitters are also contemplated herein as will be understood by those of ordinary skill in the art.

In some embodiments, the reaction system may include a disposable reaction container comprising a wall having exterior and interior surfaces surrounding a reaction chamber, the interior surface being directly adjacent to the reaction chamber; one or more fluidic channels (or pathways) extending into the reaction chamber through the wall; the fluidic channel comprising multiple fluidic exits and terminating in a closed end. As the fluidic channel terminates in a close end, fluid flowing through the fluidic channel exits the same through the fluidic exits. In some embodiments, the fluidic channel may be or comprise tubing comprising fluidic exits (e.g., as holes in the walls of the tubing). In some embodiments, the fluid exits the fluidic channel under sufficient pressure to cause the fluid to contact the interior surface by, e.g., spraying outwards towards the same. In some embodiments, the closed end is formed by, e.g., fused walls of the fluidic channel or a cap covering the end of the fluidic channel. In some embodiments, the fluidic exits are positioned approximately centrally within the reaction chamber relative to the interior surface. In some embodiments, the fluidic exits within the reaction chamber are distributed relatively evenly along the fluidic channel. In some embodiments, the fluidic exits are arranged to distribute fluid from the fluidic channel at various angles; and/or to distribute the fluid away from the fluidic channel in substantially all perpendicular and/or upward directions, and/or substantially all directions. In some embodiments, the reaction chamber is at least partially spherical (e.g., forming a shape such as dome (e.g., resembling the hollow upper half of a sphere)). In some embodiments, the fluid flowing through the fluidic channel is a cleaning solution. In some embodiments, the flow of fluid into the fluidic channel and/or the reaction chamber is regulated by a control system, such as an automated control system (e.g., using software). Exemplary reaction systems for which these embodiments may be suitable include but are not limited to any described herein (e.g., reaction systems comprising first and second zones (e.g., a headspace)), any described in U.S. Pat. No. 8,658,419 B2; U.S. Pat. No. 9,228,165 B2; and/or U.S. Pat. Pub. No. 2016/0272931 A1, each of which being hereby incorporated in their entireties into this disclosure. Other embodiments comprising such fluid channel structures are also contemplated herein as will be understood by those of ordinary skill in the art.

Figure 4:
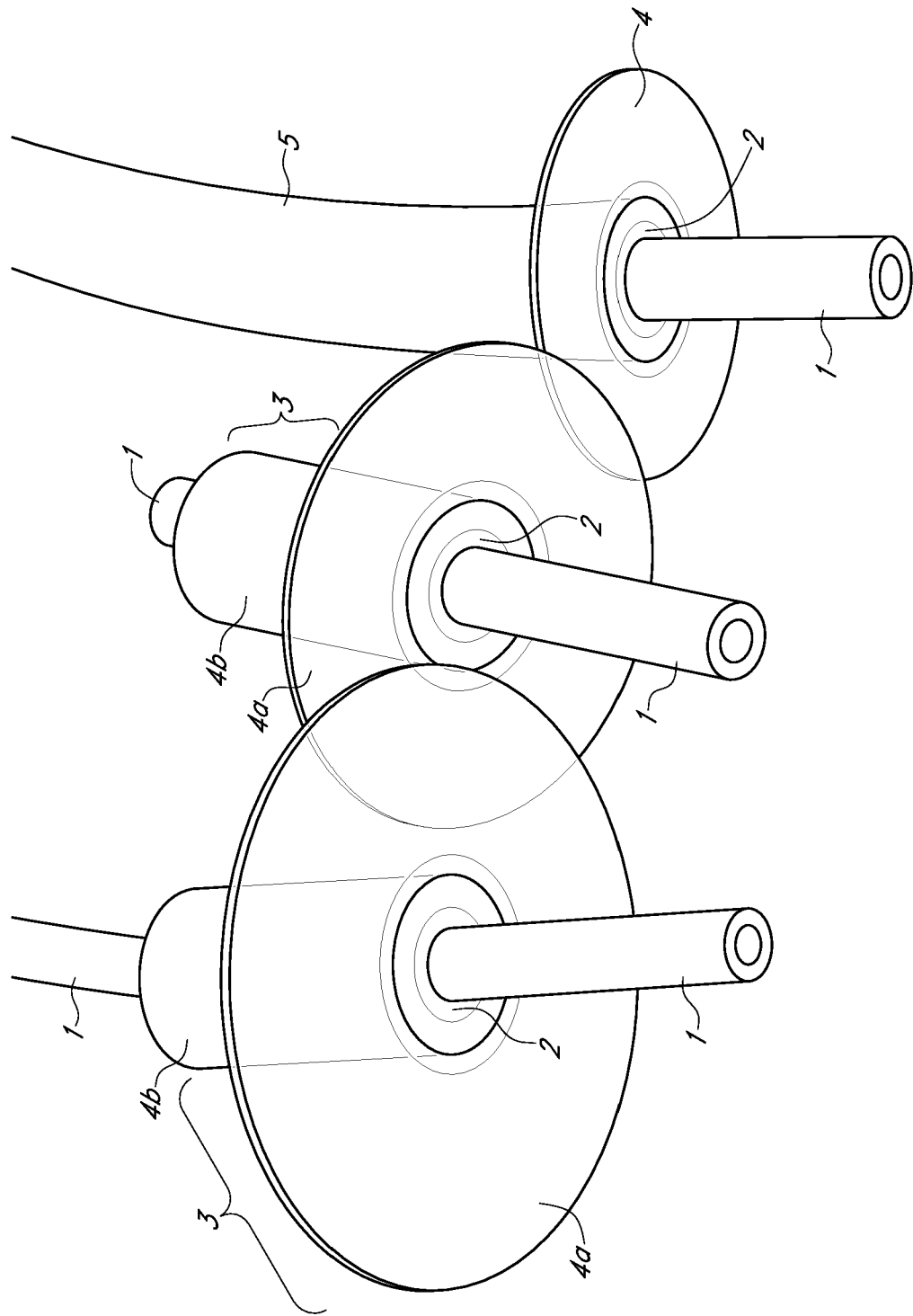
FIG. 4 illustrates three exemplary embodiments of a low/high pH-compatible fluidic channel adjoined to a polyolefin port.

Acid and base are routinely added to reactor systems (e.g., fermenters, bioreactors, and the like) to adjust pH between pH 2.5 and 11 in order to carry out certain processes such as, e.g., to digest cells, inactivate viruses, or for chemical decontamination of such systems (e.g., from microbes or active agents). In some embodiments, a strong acid or base may need to be used to treat (e.g., clean) the reaction chamber. Typical materials such as polyethylene films and polyolefin ports are understood by those of ordinary skill in the art to be compatible (e.g., structurally stable) with solutions having a pH of from 2.5 to 11, with only limited supporting data as to the pH at which such materials actually fail. There is a need in the art for reactor systems suitable for use with solutions having a pH of from zero to 14. In some embodiments, then, the above described one or more fluidic channels and related structures (e.g., ports) are chemically compatible (e.g., structurally stable) with solutions having a pH of from zero to 14 (referred to herein as "low/high pH compatibility"). Exemplary materials that can provide such low/high pH compatibility include a thermoplastic elastomer (TPE) such as, for instance, a mixture comprising a thermoplastic elastomer (e.g., at least about 20% wt %) and polyolefin (less than about 50% wt), optionally further comprising styrene, and/or as described in U.S. Pat. No. 9,334,984 B2 (Siddhamalli, et al.) An exemplary low/high pH compatible tubing that can be used as described herein is the commercially available C-Flex® tubing (Saint-Gobain Performance Plastics Corp., e.g., comprising any of formulations 374, 082, or 072). In some embodiments, the acid or base solution may be maintained in a low/high pH-compatible container (e.g., a glass container) and delivered to the reaction chamber through a high/low pH compatible fluidic channel (e.g., tubing comprised of a TPE). The low/high pH compatible fluidic channel can extend through a port comprised of a low/high pH-incompatible material (e.g., a polyolefin port) leading from the exterior to the interior of the reaction chamber, or it can be flush with the end of the port opening into the reaction chamber such that the low/high pH-incompatible material comprising the port (e.g., a polyolefin) is not contacted by the high/low pH solution. In some embodiments, the polyolefin port can include a disc-shaped surface having a diameter wider than that of the fluidic channel (see, e.g., FIG. 4). FIG. 4 illustrates exemplary arrangements of a low/high pH-compatible fluidic channel (e.g., tube) (1) within a larger diameter tube that is typically comprises of a material that is not low/high pH-compatible (i.e., a material that is low/high pH-incompatible) (2). In FIG. 4, the low/high pH-compatible tube (1) and the low/high pH-incompatible tubing (2) is shown with a port structure (3 including port disc 4a and port neck 4b). In some embodiments, the port may comprise a port disc (4a) an extended neck (5) that effectively serves as the outside tube (that with a diameter larger than the low/high pH-compatible fluidic channel/tube). The low/high pH-compatible tube (1) is typically connected to a source of the low or high pH solution that is to be deposited into the reaction chamber through the low/high pH-compatible tube (1). Using this arrangement, the high/low pH solution can then be deposited into the reaction chamber and any fluid contained therein (e.g., reactants left over after reaction is complete) without contacting and/or damaging the pH-incompatible parts of the reactor system. Fluid contained within the reaction chamber (including that after addition of the low or high pH solution) is maintained at a pH compatible with the material of which the disposable container is comprised (e.g., the material surrounding or forming the reaction chamber). Such a compatible pH is typically from about 2.5 to about 11 (e.g., an acceptable set/control point). These modifications to the systems described herein allow for the passage of low/high pH solutions (i.e., below pH 2.5 or above pH 11) from a source container to the reaction chamber without the risk of material failure due to pH-incompatibility. Thus, is some embodiments, the disposable reaction systems described herein can include a fluidic channel, and optionally some or preferably all tubing leading to the fluidic channel and/or reaction chamber, comprised of a material that remains structurally intact in the presence of a fluid having a pH of between zero and 14. In some embodiments, the material is or comprises a thermoplastic elastomer. Other arrangement of such parts, and similar parts, and other low/high pH-compatible materials, are also contemplated herein as would be understood by those of ordinary skill in the art.

One or more low/high pH-compatible tubes (e.g., fluidic channels) may be prepared and included in tubing sets for use in the low/high pH solution delivery system (e.g., "tube-sets", "tube-within-a-tube" system; see, e.g., the exemplary embodiments illustrated in FIG. 4). For example, a first fluidic channel (e.g., tube) comprised on a low/high pH-compatible material (e.g., a material is stable in a pH range of from 0-14) may be inserted into or constructed within (e.g., over-molding) second fluidic channel (e.g., tube) that is not comprised of a low/high pH-compatible material (e.g., a material is not stable in a pH range of from 0-14). In some embodiments, such tube-sets may be constructed by, for example: constructing an over-molded part (over-molding the inner diameter (ID) of an outer tube to the outer diameter (OD) of an inner tube), and inserting the inner tube through the port (leading to the reaction chamber) where the outer hose is positioned over the inner hose and the barb (where present). In some embodiments, such tube-sets may be constructed by, for example constructing an over-molded part, inserting an inner tube (e.g., hose) through the port comprised of a low/high pH-incompatible material such that the outer tubing (e.g., hose) is positioned over the inner tube (e.g., hose) and over the barb, filling the annular space with resin and melting the same to achieve flow/sealing of the two tubes (e.g., thereby filling the annular space). Other methods for manufacturing such pH-compatibility systems are also contemplated herein as would be understood by those of ordinary skill in the art.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. The term "maintain" with respect to temperatures is not meant to indicate that a particular temperature remains the same over any particular time period. It should be understood that a temperature "maintained" at a particular level will vary over time by, for example 0.1-10%, such as about any of 1%, 5%, or 10%. "Fixably attached", "affixed", or "adjoined" means that at least two materials are bonded to one another in a substantially permanent manner. The various parts described herein may be bonded to one another using, for example, welding, using an adhesive, another similar process, and/or using connectors such as tubing. The parts must remain attached to one another during use, meaning that the points of attachment (e.g., boundaries, joints) between the parts must be able to withstand the hydraulic and other forces encountered within the reaction vessel and between the parts due to, e.g., the motion of the reactor contents in response to the action of the agitator mechanism in addition to the pressures created from the heat transfer media flow. "Optional" or "optionally" means that the subsequently described event or circumstance can or cannot occur, and that the description includes instances where the event or circumstance occurs and instances where it does not. Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed. The term "on" and "upon", unless otherwise indicated, means "directly on or directly connected to the other element" (e.g., two parts of the systems described herein). The term "adjacent to" may refer to an indirect connection between two elements such as parts of the systems described herein.

A "fluidic pathway" is a pathway withing the systems described herein (e.g., a channel) through which one or more fluids (e.g., a gas or liquid) can migrate and/or can be transported and/or moved through. A "fluidic connection" or to be "in fluidic communication" refers to at least two parts of the systems described herein through which fluid may directly and/or indirectly flow (e.g., as a fluid may move from a disposable reaction container into a coalescer, and/or vice-versa, thus the disposable reaction container and coalescer share a "fluidic connection" and are in "fluidic communication" with one another). A "fluid pathway" or "fluidic pathway" or "fluidic channel" is a pathway as commonly understood by those of ordinary skill in the art (e.g., a channel) through which fluid may flow. Other similar terms in this disclosure will understood by those of ordinary skill in the art when read in its proper context.

All references cited within this disclosure are hereby incorporated by reference in their entirety. Certain embodiments have been described herein, but are provided as examples only and are not intended to limit the scope of the claims in any way. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:
1. A system comprising:
   a. a disposable reaction container contained within a reactor vessel;
   b. at least one heat transfer system;
   c. a jacketed tank head integral with the reactor vessel and being positioned above the disposable reaction container; and,
   d. a coalescer comprising an internal tortuous fluidic pathway and being positioned on the jacketed tank head;
   wherein:
      the disposable reaction container comprises a first zone comprising a reaction mixture maintained at a first temperature;
      the disposable reaction container comprises a second zone comprising a headspace above the reaction mixture into which humid gas migrating from the reaction mixture migrates;
      the second zone being at a second temperature lower than that of the first temperature; and,
      fluid migrating from the second zone coalesces within the internal tortuous fluidic channel of the coalescer.
2. The system of claim 1 wherein:
   a. the at least one heat transfer heat transfer system maintains the first zone at a first temperature;
   b. the at least one heat transfer heat transfer system maintains the second zone at a second temperature lower than the first temperature; and,
   c. fluid migrating from the headspace coalesces within the internal fluidic channel of the coalescer.
3. The system of claim 1 comprising a first heat transfer system associated with the first zone and a second heat transfer system associated with the second zone.
4. The system of claim 3 wherein:
   a) the third heat transfer system is in fluidic communication with the first and/or second heat transfer systems;
   b) wherein at least two of the heat transfer systems are contiguous with one another;
   c) at least one of the heat transfer systems is not contiguous with at least one other heat transfer system;
   d) at least two of the heat transfer systems are interconnected by a fluidic pathway, optionally wherein the second and third heat transfer system are interconnected; and,
   e) the same type of heat transfer fluid is in each heat transfer system.
5. The system of claim 1 wherein:
   a) the second zone is positioned above the first zone;
   b) the second zone is partially defined by an upper exterior surface adjacent to the jacketed tank head;
   c) the coalescer comprises upper and lower surfaces and the internal tortuous fluidic pathway is contiguous with the either of both of said upper and/or lower surfaces; and,
   d) the coalescer is comprised of at least two pieces of flexible material fused together to form a chamber comprising the internal tortuous fluidic pathway,
   wherein:
      i) the internal tortuous fluidic pathway is defined by fused sections of the at least two pieces of flexible material; or,
      ii) the internal tortuous fluidic pathway is defined by a third material contained within the chamber.
6. The system of claim 1 further comprising at least one anti-foam device positioned between the disposable reaction container and the coalescer.
7. The system of claim 1 comprising at least one baffle comprising a first sub-assembly consisting essentially of a first material adjoined to a second material to form a first distribution channel; a second sub-assembly consisting essentially of a first material adjoined to a second material to form a second distribution channel; and, a relief channel between the first sub-assembly and the second sub-assembly; optionally wherein at least one such baffle is associated with the first zone and a separate such baffle is associated with the second zone.

8. The system of claim 1 comprising multiple coalescers, optionally wherein:
   a) the coalescers are not interconnected through one or more fluidic pathways;
   b) one or more of each coalescers is associated with at least one anti-foam device;
   c) each coalescer comprises a lower surface in contact with the jacketed tank head; and/or
   d) the coalescer:
      i. comprises a flexible container comprising a tortuous fluid pathway;
      ii. comprises a flexible, semi-rigid, or rigid tubular form providing for cyclonic removal of gas from the headspace; and/or,
      iii. comprises a container comprising mesh and/or packed solids.

9. The system of claim 1, further comprising an exhaust pump, optionally wherein:
   a. tubing connects the exhaust pump downstream of a sterile barrier filter in fluidic communication with the disposable reaction container;
   b. tubing connects the exhaust pump to the coalescer and an inlet or an outlet of a sterile barrier in fluidic communication with the disposable reaction container;
   c. the exhaust pump comprises variable speed control and being optionally operably linked to instrumentation for maintaining DC pressure;
   d. a first fan, optionally located on the condenser, draws exhaust gas from the headspace through the coalescing device and into or through a downstream sterile barrier; and/or,
   e. optionally at least a second fan recirculating exhaust gas within the condenser headspace and/or coalescing device.

10. The system of claim 1 wherein:
   a) the jacketed tank head physically supports the disposable reaction container; or
   b) the system comprises a heat transfer system at least partially directly in direct contact with the exterior of the second zone and at least partially not positioned within the reaction vessel; or
   c) the reaction container comprises a first zone comprising a reaction mixture maintained at a first temperature; a second zone comprising a headspace above the reaction mixture into which humid gas migrating from the reaction mixture can migrate; and at least one diaphragm pressure transmitter, load cell, and/or scale in contact with the second zone;
   and optionally wherein:
      the diaphragm pressure transmitter, load cell, and/or scale comprises a membrane for detecting pressure in contact with the reaction container; and/or
      the diaphragm pressure transmitter, load cell, and/or scale detects the pressure exerted upon the reaction container by gases and fluids present in the second zone; and/or
      the diaphragm pressure transmitter, load cell, and/or scale contacts the exterior surface of the reaction container; and/or
      the diaphragm pressure transmitter, load cell, and/or scale is in communication with a control system for adjusting the pressure within the second zone in response to information received from diaphragm pressure transmitter, optionally wherein the control system continuously monitors information generated by the diaphragm pressure transmitter, load cell, and/or scale and adjusts the pressure within the second zone using an exhaust pump; and/or
      the control system is automated.

11. A system of claim 1 wherein the disposable reaction container comprises exterior and interior surfaces; the interior surface surrounding a reaction chamber; a fluidic channel extending into the reaction chamber; the fluidic channel comprising multiple fluidic exits and a closed end; wherein fluid flowing through the fluidic channel and exits the same through the fluidic exits under sufficient pressure to cause the fluid to contact the interior surface.

12. The system of claim 11 wherein:
   the closed end is formed by terminal fused walls of the fluidic channel or a cap covering the end of the fluidic channel; and/or
   the fluidic exits are positioned approximately centrally within the reaction chamber relative to the interior surface; and/or
   the reaction chamber is at least partially spherical; and/or
   the fluidic exits are distributed relatively evenly along the fluidic channel within the reaction chamber; and/or
   the fluidic exits are arranged to distribute fluid from the fluidic channel at various angles; and/or to distribute the fluid away from the fluidic channel in substantially all perpendicular and/or upward directions, and/or substantially all directions; and/or
   the fluid flowing through the fluidic channel is a cleaning solution; and/or
   the fluidic channel, and optionally any tubing leading to the fluidic channel and/or reaction chamber, is comprised a material that remains structurally intact in the presence of a fluid having a pH of between zero and 14 and optionally wherein the material is a thermoplastic elastomer.

13. The system of claim 3 further comprising a third heat transfer system provided by the jacketed tank head.

14. The system of claim 1 wherein the jacketed tank head comprises a fluidic channel through which a heat transfer fluid may be circulated.

15. The system of claim 13 wherein the jacketed tank head comprises a fluidic channel through which a heat transfer fluid may be circulated.

* * * * *